(12) United States Patent
Dwivedi et al.

(10) Patent No.: US 9,012,678 B2
(45) Date of Patent: Apr. 21, 2015

(54) PROCESSES FOR THE PREPARATION OF FESOTERODINE

(75) Inventors: Shriprakash Dhar Dwivedi, Gujarat (IN); Ashok Prasad, Gujarat (IN); Kuldeep Natwarlal Jain, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 17 days.

(21) Appl. No.: 13/818,791

(22) PCT Filed: Aug. 25, 2011

(86) PCT No.: PCT/IN2011/000575
§ 371 (c)(1),
(2), (4) Date: Apr. 16, 2013

(87) PCT Pub. No.: WO2012/025941
PCT Pub. Date: Mar. 1, 2012

(65) Prior Publication Data
US 2013/0197260 A1    Aug. 1, 2013

(30) Foreign Application Priority Data

Aug. 25, 2010 (IN) .......................... 2373/MUM/2010
Nov. 16, 2010 (IN) .......................... 3128/MUM/2010
Mar. 17, 2011 (IN) ............................ 761/MUM/2011

(51) Int. Cl.
| | |
|---|---|
| C07C 69/76 | (2006.01) |
| C07C 219/28 | (2006.01) |
| C07C 41/26 | (2006.01) |
| C07C 51/43 | (2006.01) |
| C07C 59/56 | (2006.01) |
| C07C 67/03 | (2006.01) |
| C07C 213/10 | (2006.01) |
| C07C 217/62 | (2006.01) |
| C07C 309/66 | (2006.01) |
| C07C 213/00 | (2006.01) |
| C07C 213/06 | (2006.01) |
| C07C 213/08 | (2006.01) |
| C07C 303/28 | (2006.01) |
| C07C 309/67 | (2006.01) |

(52) U.S. Cl.
CPC ............... *C07C 219/28* (2013.01); *C07C 41/26* (2013.01); *C07C 51/43* (2013.01); *C07C 59/56* (2013.01); *C07C 67/03* (2013.01); *C07C 213/10* (2013.01); *C07C 217/62* (2013.01); *C07C 309/66* (2013.01); *C07C 213/00* (2013.01); *C07C 213/06* (2013.01); *C07C 213/08* (2013.01); *C07C 303/28* (2013.01); *C07C 309/67* (2013.01); *C07B 2200/07* (2013.01); *C07B 2200/13* (2013.01)

(58) Field of Classification Search
CPC ..... C07C 213/10; C07C 219/28; C07C 41/26; C07C 51/43; C07C 59/56; C07C 67/03; C07C 213/00; C07C 213/06; C07C 213/08; C07C 215/54; C07C 217/62; C07C 303/28; C07C 309/66; C07C 309/67; C07C 43/23; C07C 69/734; C07B 2200/07; C07B 2200/13
USPC .......... 356/51; 558/44; 560/60, 252; 564/443
See application file for complete search history.

(56) References Cited

U.S. PATENT DOCUMENTS

| | | | |
|---|---|---|---|
| 6,713,464 B1 * | 3/2004 | Meese et al. ................... | 514/175 |
| 6,858,650 B1 * | 2/2005 | Meese ............................ | 514/530 |
| 8,530,691 B2 * | 9/2013 | Mantegazza et al. ........... | 560/42 |
| 2010/0120031 A1 | 5/2010 | Appella et al. | |
| 2011/0086103 A1 * | 4/2011 | Charugundla et al. ........ | 424/489 |
| 2011/0171274 A1 | 7/2011 | Neela et al. | |
| 2012/0107794 A1 | 5/2012 | Appella et al. | |

FOREIGN PATENT DOCUMENTS

| | | | |
|---|---|---|---|
| JP | 2006213635 | * | 8/2006 |
| WO | WO2005012227 | * | 2/2005 |
| WO | WO2007144091 | * | 12/2007 |
| WO | WO 2008/039367 | | 4/2008 |
| WO | WO2009037569 | * | 3/2009 |
| WO | WO 2009/122303 | | 10/2009 |
| WO | WO 2010/010464 | | 1/2010 |

OTHER PUBLICATIONS

Rohm and Haas 2008.*
JP2006 (translation JP2006 from a website titled "AIPN Japan Patent Office" The translation was conducted on May 20, 2014).*
Non-final for U.S. Appl. No. 13/818,791 mailed Jun. 24, 2014.*
International Search Report for PCT/IN2011/000575 mailed Jul. 30, 2012.
Y. Kobayashi et al., "Hydrogen-Bonding Sheets in Crystals for Chirality Recognition: Synthesis and Application of (2S,3S)-2,3-dihydroxy-and (2S,3S)-2,3-Dibenzyloxy-1,4-bis (hydroxyami no) Butanes", Tetrahedron Asymmetry. vol. 19, No. 21, Nov. 3, 2008, pp. 2536-2541.

* cited by examiner

*Primary Examiner* — Yong Chu
*Assistant Examiner* — Blaine G Doletski
(74) *Attorney, Agent, or Firm* — Nixon & Vanderhye P.C.

(57) ABSTRACT

The invention relates to improved process for the preparation of fesoterodine and its pharmaceutically acceptable salt, specifically fesoterodine fumarate of formula (1). The invention relates to solid state forms of a novel salt of fesoterodine and process for the preparation thereof. The invention also relates to highly pure fesoterodine fumarate substantially free of impurity X at RRT 1.37. The invention also provides solid particles of pure fesoterodine fumarate wherein 90 volume-percent of the particles (D90) have a size of higher than 200 microns.

7 Claims, 7 Drawing Sheets

PROCESSES FOR THE PREPARATION OF FESOTERODINE

This application is the U.S. national phase of International Application No. PCT/IN2011/000575 filed 25 Aug. 2011 which designated the U.S. and claims priority to IN 2373/MUM/2010 filed 25 Aug. 2010, IN 3128/MUM/2010 filed 16 Nov. 2010, and IN 761/MUM/2011 filed 17 Mar. 2011, the entire contents of each of which are hereby incorporated by reference.

FIELD OF THE INVENTION

The invention relates to improved process for the preparation of fesoterodine and its pharmaceutically acceptable salt, specifically fesoterodine fumarate of formula (1). The invention relates to solid state forms of a novel salt of fesoterodine and process for the preparation thereof. The invention also relates to highly pure fesoterodine fumarate substantially free of impurity X at RRT 1.37. The invention also provides solid particles of pure fesoterodine fumarate wherein 90 volume-percent of the particles (D90) have a size of higher than 200 microns.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Fesoterodine fumarate is the international non-proprietary name (INN) of the active ingredient isobutyric acid 2-[(R)-3-diisopropylammonium-1-phenylpropyl)-4-(hydroxy-methyl)phenyl ester hydrogen fumarate, which can be represented by the structural formula (1)

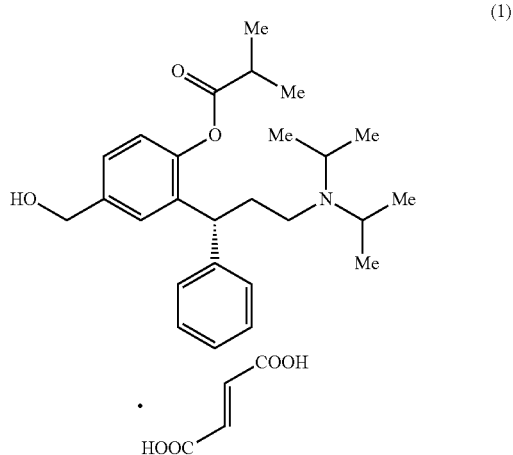

Fesoterodine fumarate is approved in Europe and USA for the treatment of overactive bladder syndrome with the commercial name TOVIAZ®.

U.S. Pat. No. 6,713,464 B1 discloses a variety of 3,3-diphenylpropylamine derivatives, processes for their preparation, pharmaceutical compositions comprising the derivatives, and methods of use thereof. These compounds are anti-muscarinic agents with superior pharmacokinetic properties compared to existing drugs such as oxybutynin and tolterodine which are useful in the treatment of urinary incontinence, gastrointestinal hyperactivity (irritable bowel syndrome) and other smooth muscle contractile conditions.

Improved processes for the preparation of fesoterodine and its pharmaceutically acceptable salts are disclosed in US Patent application 2009/0306384 A1, and International (PCT) Publication No. WO 2009/037569 A2.

U.S. Patent Application No. 2010/0168459 A1 dislcoses the use of N,N-diisopropylethyl amine for the condensation of diol compound and isobutyryl chloride for the ultimate formation Fesoterodine free base.

U.S. Patent Application No. 2010/174107 A1 discloses use of Turbo Grignard reagent of formula $R^1(MgX)n.LiY$, wherein $R^1$ is an aromatic, aliphatic, carbocyclic or heterocyclic organic group having 1 to 24 carbon atoms; X and Y are independently selected from Cl, Br and I and n is 1 or 2, for the formation of protected ester from the bromo protected compound as shown in Scheme-1 (wherein simple Grignard reagent is used).

International (PCT) Publication No. WO 2009/044278 A1 of relates to amorphous Fesoterodine fumarate being characterized by XRPD & IR.

International (PCT) Publication No. WO 2009/122303 A1 discloses preparation of Fesoterodine mandelate salt.

International (PCT) Publication No. WO 2010/010464 A2 discloses an impurity of fesoterodine i.e., fesoterodine dehydroxy impurity.

US patent application No. 2010/0152483 A1 discloses Fesoterodine fumarate in crystalline Form—I being characterized by XRPD, DSC, IR, $^{13}C$ NMR and Raman spectra. US Patent application also discloses Amorphous Fesoterodine Fumarate being characterized by XRPD and IR.

U.S. Pat. No. 6,858,650 describes various acid addition salts of 3,3-dipbenylpropylamine derivatives.

The references cited in the above art for the preparation of Fesoterodine fumarate (I) involves reaction conditions, which leads to formation of side reactions and byproducts. Processes disclosed in the art involve the formation of intermediates as an oil or syrup with low yield and purity.

PCT application WO 2010010464 A2 discloses the process for obtaining fesoterodine fumarate having a 90 volume-percent of the particles ($D_{90}$) with a size of less than or equal to about 200 microns and process for achieving the particle size ($D_{90}$) with a size of less than or equal to about 200 microns.

It is reported in the literature that fesoterodine may exhibit substantial degradation in a humid environment and at increased temperature. It is believed that hydrolyzation and oxidation are among the major mechanisms resulting in degradation. Therefore, it is desired to develop a fesoterodine fumarate, which is stable under stress condition. It has been found, surprisingly, that fesoterodine fumarate with higher particle size significantly slow down the degradation of fesoterodine under stress conditions.

SUMMARY OF THE INVENTION

In one general aspect there is provided a 2-chloro-mandelate salt of fesoterodine. The 2-chloro-mandelate salt of fesoterodine may exist in a crystalline form or an amorphous form. The 2-chloro-mandelate salt of fesoterodine may have the X-ray diffraction pattern of FIG. 5, differential scanning calorimetry thermogram og FIG. 6, and infrared spectrum of FIG. 7.

In another general aspect there is provided a process for the preparation of 2-chloro-mandelate salt of fesoterodine. The process includes obtaining a solution of fesoterodine in one or more solvents; contacting the solution with 2-chloro-mandelic acid; and isolating the 2-chloro-mandelate salt of fesoterodine by the removal of solvents.

Removing the solvents may include, for example, one or more of filtration, filtration under vacuum, decantation, centrifugation, distillation and distillation under vacuum.

In one general aspect, the solution may be cooled before the removal of solvents to obtain better yields. The process may include further drying of the product obtained.

The process may produce the pure 2-chloro-mandelate salt of fesoterodine having purity more than 99% by HPLC. In particular, it may produce the pure 2-chloro-mandelate salt of fesoterodine having purity more than 99.5% by HPLC.

The pure 2-chloro-mandelate salt of fesoterodine may be converted into pure fesoterodine by treatment with a base.

In another general aspect there is provided a process for the preparation of substantially pure fesoterodine and its pharmaceutically acceptable salts. The process includes contacting fesoterodine with 2-chloro-mandelic acid in one or more solvents; isolating 2-chloro-mandelate salt of fesoterodine; treating the 2-chloro-mandelate salt of fesoterodine with a base; isolating the substantially pure fesoterodine by the removal of solvents; and optionally, converting the substantially pure fesoterodine into its pharmaceutically acceptable salt.

Removing the solvents may include, for example, one or more of filtration, filtration under vacuum, decantation, centrifugation, distillation and distillation under vacuum.

The process may include further drying of the product obtained.

The process may produce the substantially pure fesoterodine having purity more than 99% by HPLC. In particular, it may produce the pure fesoterodine having purity more than 99.5% by HPLC.

In another general aspect there is provided a process for the preparation of stable fesoterodine fumarate. The process includes obtaining a solution of substantially pure fesoterodine in one or more solvents; treating the solution with fumaric acid; and isolating the stable fesoterodine fumarate by the removal of solvents.

Embodiments of the process may include one or more of the following features. For example, the solution of fesoterodine may be obtained by heating fesoterodine in one or more solvents or the solution may be heated prior to treatment with fumaric acid. The solution may be seeded with one or more crystals of fesoterodine fumarate prior to the initiation of product crystallization or the slurry may be cooled prior to filtration.

In one general aspect a second solvent may be added resulting in the precipitation of the stable fesoterodine fumarate and removing the solvent there from by filtration, filtration under vacuum, decantation, or centrifugation.

The details of one or more embodiments of the invention are set for the in the description below. Other features, objects and advantages of the invention will be apparent from the description and claims.

BRIEF DESCRIPTION OF THE ACCOMPANYING DRAWINGS

FIG. 1: X-ray diffraction pattern of crystalline 3-(2-(benzyloxy)-5-bromophenyl)-3-phenyl propyl methanesulfonate of formula (D).

FIG. 2: Differential Scanning calorimetry of crystalline 3-(2-(benzyloxy)-5-bromophenyl)-3-phenylpropyl methanesulfonate of formula (D).

FIG. 3: Differential Scanning calorimetry of crystalline Fesoterodine Fumarate (1).

FIG. 4: Infrared spectrum of crystalline Fesoterodine Fumarate (1).

DETAILED DESCRIPTION OF THE INVENTION

As used herein, the term "stable fesoterodine fumarate" fesoterodine fumarate containing any individual impurities less than 0.15% after exposure to a relative humidity of 60% at 25° for a period of at least three months or after exposure to a relative humidity of 75% at 40° for a period of at least three months As used herein the term "substantially pure fesoterodine 2-chloro-mandelate" refers to the fesoterodine 2-chloro-mandelate having a purity of greater than about 99 wt %, specifically greater than about 99.5 wt %, more specifically greater than about 99.8 wt %, and still more specifically greater than about 99.9 wt %.

The invention provides a process for preparation of fesoterodine and its pharmaceutically acceptable salt In further embodiments, the invention provides fesoterodine 2-chloro-mandelate salt. The fesoterodine 2-chloro-mandelate is useful as an intermediate in the preparation and purification of fesoterodine free base, or a pharmaceutically acceptable salt thereof. The invention further provides a process for preparing fesoterodine 2-chloro-mandelate salt.

The invention provides fesoterodine salt with 2-chloro-mandelic acid. The 2-chloro-mandalic acid can be selected from racemic (±)2-chloro-mandelic acid, S-(+)-2-chloro-mandelic acid or R-(−)-2-chloro-mandelic acid.

In general, S-(+)-2-chloro-mandelic acid or R-(−)-2-chloro-mandelic acid, when used for salt formation, it consist more than 60% chiral purity. However, the chiral purity should not be considered as limiting the scope of the invention.

In another aspect, there is provided a solid state form of fesoterodine salt with 2-chloro-mandelic acid. The solid state form of fesoterodine 2-chloro-mandelate can exists in an amorphous form or a crystalline form.

In another embodiment, the solid state form of fesoterodine 2-chloro-mandelate exists in an anhydrous and/or solvent-free form or as a hydrate and/or a solvate form. Such solvated or hydrated forms may be present as hemi-, mono-, sesqui-, di- or tri-solvates or hydrates.

Figure 1:
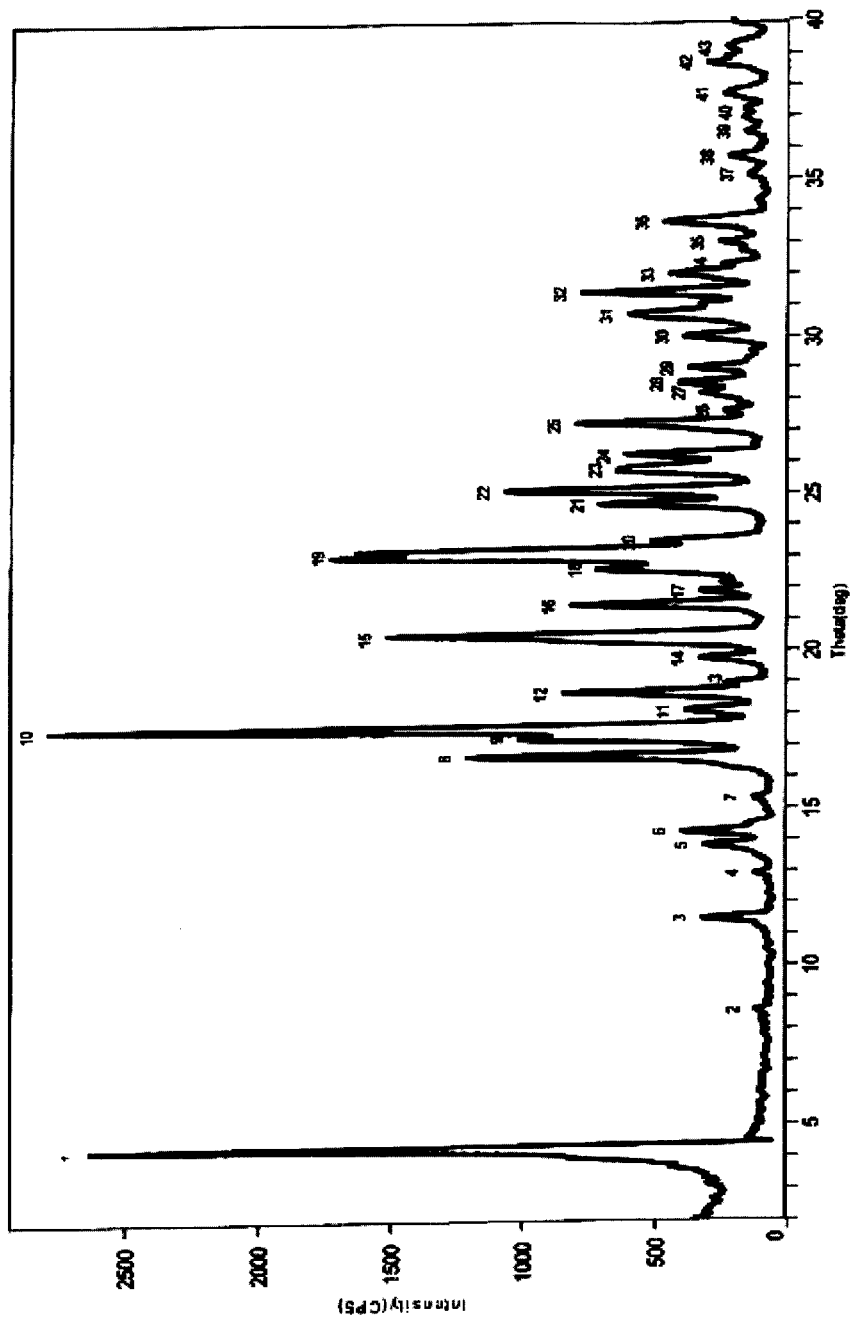
Figure 5:
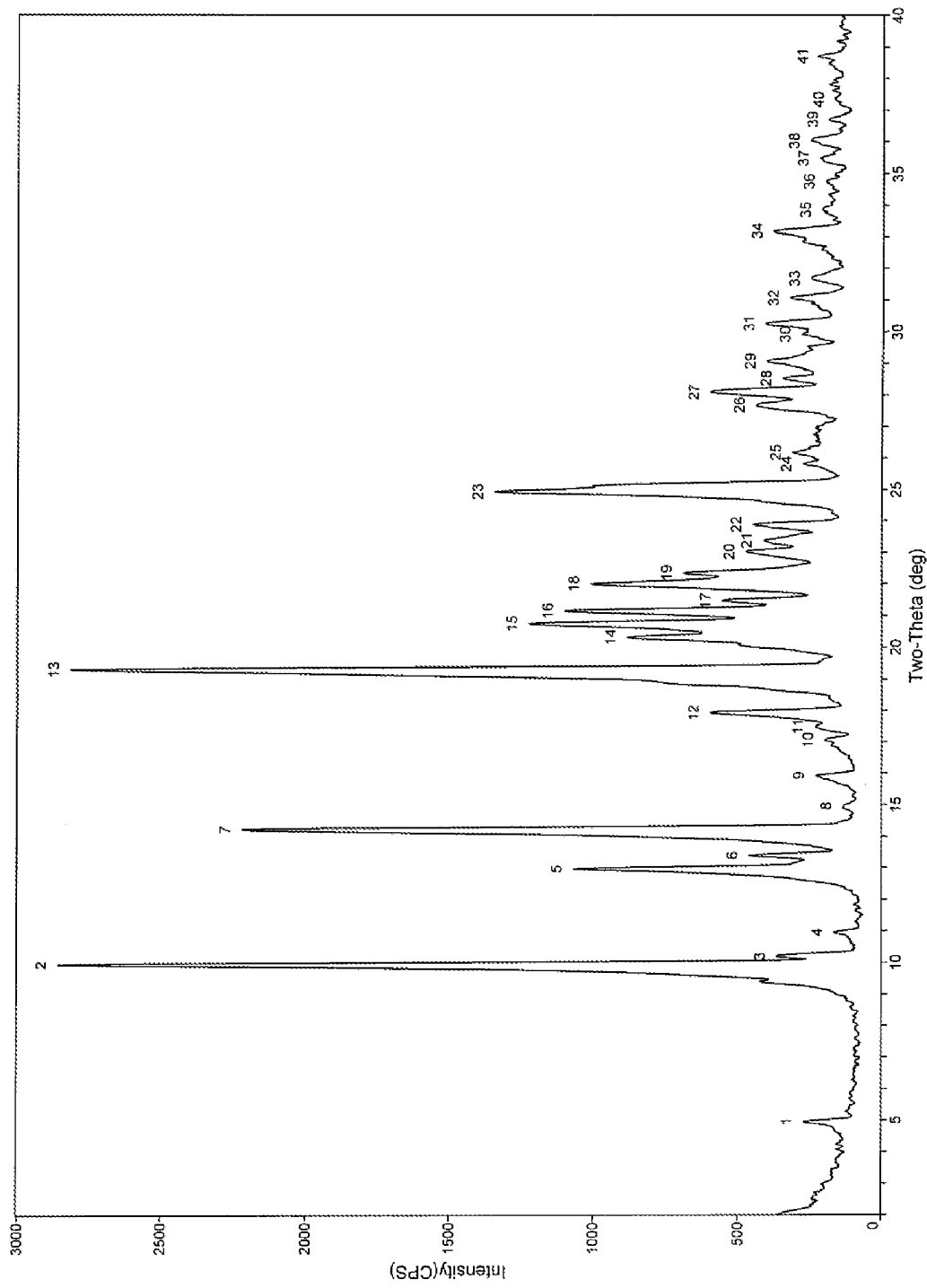
FIG. 5 is a characteristic powder X-ray diffraction (XRD) pattern of Fesoterodine 2-Chloro-mandelate.
Figure 6:
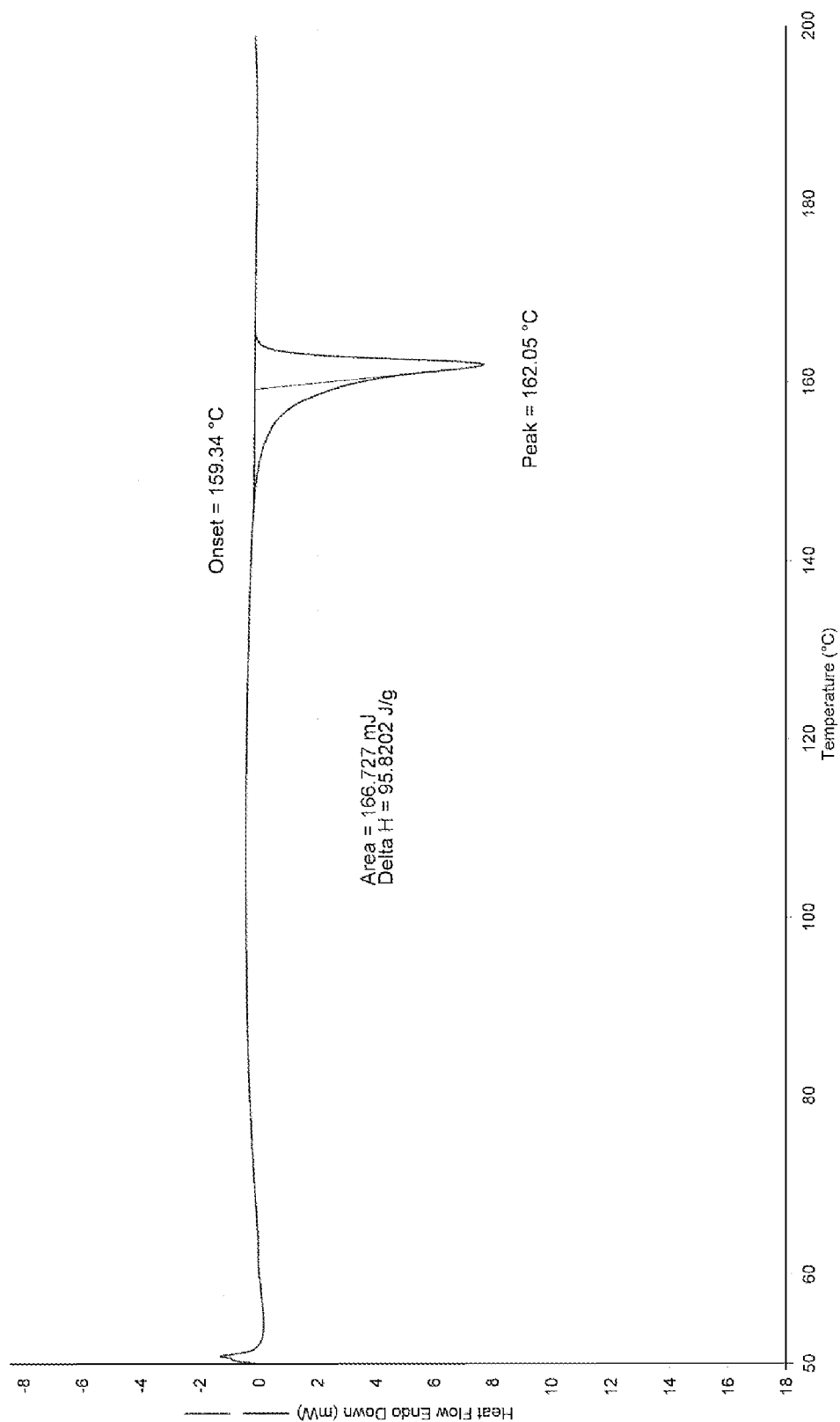
FIG. 6 is a characteristic differential scanning calorimetry (DSC) thermogram of Fesoterodine 2-Chloro-mandelate.
Figure 7:
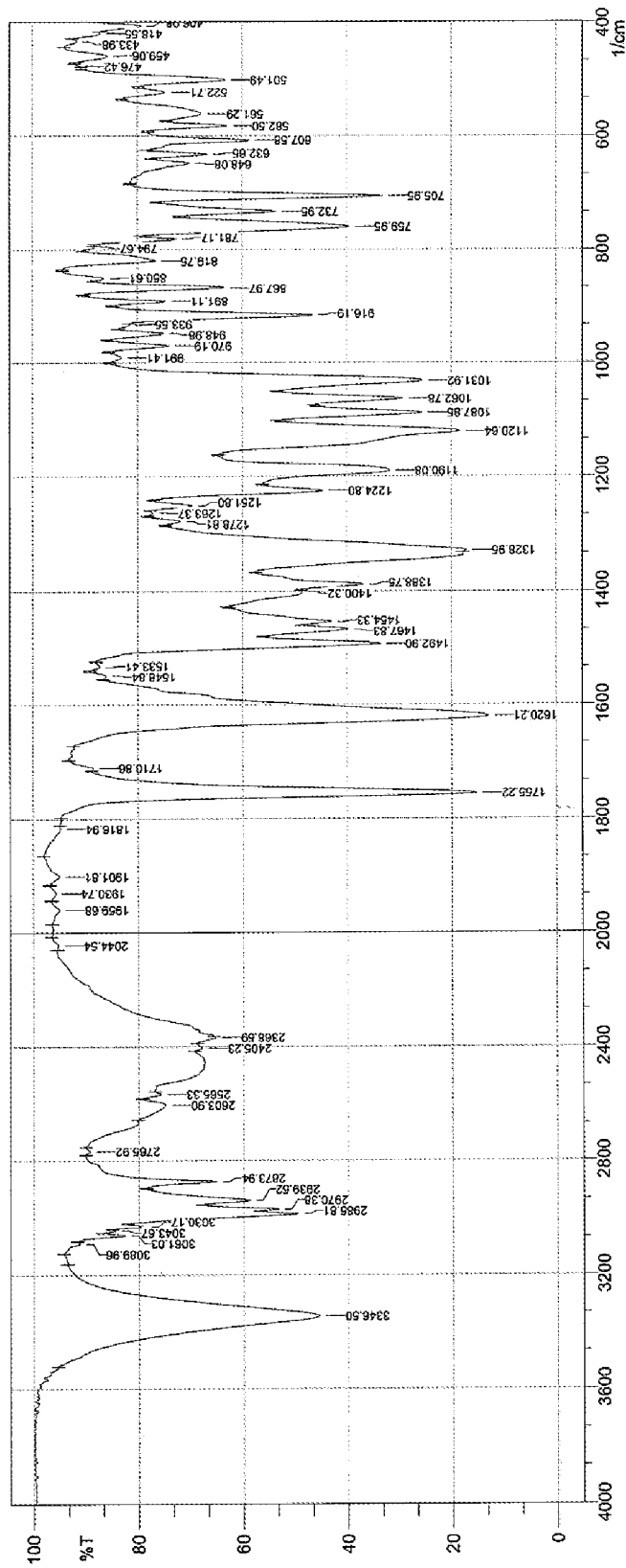
FIG. 7 is a characteristic infra red (IR) spectrum of Fesoterodine 2-Chloro-mandelate.

According to another aspect, the fesoterodine (S)-(+)-2-chloro-mandelate is characterized by at least one, or more, of the following properties:
i) a powder X-ray diffraction pattern having peaks at about 9.9, 12.9, 14.2, 19.2, 20.7 and 24.9±0.2 degrees 2-theta;
ii) a powder X-ray diffraction pattern having additional peaks at about 4.9, 10.2, 13.3, 15.9, 17.9, 20.3, 21.1, 21.9, 22.3, 23.8, 27.6, 28.1, 29.0, 30.2, and 33.1±0.2 degrees 2-theta substantially as depicted in FIG. 1;
iii) a powder X-ray diffraction pattern substantially as depicted in FIG. 5
iv) a DSC thermogram having an endotherm peak at about 162° C. substantially as depicted in FIG. 6
v) an IR spectrum substantially in accordance with FIG. 7; and vi) an IR spectrum having absorption bands at about 3346, 2985, 2970, 2939, 2873, 2603, 2368, 1755, 1620, 1492, 1388, 1328, 1224, 1190, 1120, 1087, 1062, 1031, 970, 916, 867, 819, 759, 732, 705, 607, 582. 561, 522 and 501±2 cm$^{-1}$.

The fesoterodine-2-chloro-mandelate is stable, consistently reproducible, and is particularly suitable for bulk preparation and handling. Moreover, fesoterodine-2-chloro-mandelate is a useful intermediate in the preparation of fesoterodine free base or a pharmaceutically acceptable salt thereof, preferably fesoterodine fumarate, in high purity.

In general, the invention provides process for preparation of fesoterodine 2-chloro-mandelate, which comprises treating fesoterodine with 2-chloro-mandelic acid in one or more organic solvent and isolating solid state form of fesoterodine salt with 2-chloro-mandelic acid.

There is provided a process for the preparation of fesoterodine 2-chloro-mandelate salt, comprising:
a) providing a first solution of fesoterodine free base in an organic solvent;
b) combining the solution with 2-chloro-mandelic acid
c) isolating fesoterodine 2-chloro-mandelate.

Exemplary organic solvents used in 2-chloro-mandelate salt formation includes, but are not limited to alcohols, ketones, chlorinated hydrocarbons, esters, nitriles, polar aprotic solvents, and mixtures thereof. The term solvent also includes mixtures of solvents.

In one embodiment, the organic solvent includes methanol, ethanol, n-propanol, isopropyl alcohol, isobutanol, n-butanol, tert-butanol, amyl alcohol, isoamyl alcohol, hexanol, acetone, methyl ethyl ketone, methyl isobutyl ketone, methyl tert-butyl ketone, acetonitrile, ethyl acetate, methyl acetate, isopropyl acetate, tert-butyl methyl acetate, ethyl formate, methylene chloride, ethylene dichloride, chloroform, N,N-dimethylformamide, N,N-dimethytacetamide, dimethylsulfoxide, and mixtures thereof; more specifically the solvent is selected from the group consisting of methanol, ethanol, isopropyl alcohol, acetone, ethyl acetate and mixtures thereof; and most specifically the solvent is ethyl acetate.

The process of preparing fesoterodine 2-chloro-mandalate includes dissolving fesoterodine in the organic solvent to obtain solution or obtaining an existing solution from a previous processing step. The solution is treated with 2-chloro-mandalate or solution of 2-chloro-mandalic acid in organic solvent. The salt formation reaction is generally carried out at room temperature to boiling point of solvent. The reaction is carried out at 25° C. to 75° C. The 2-chloro-mandelic acid used in salt formation can be used in the molar ratio of about 0.85 to 1.2 moles, specifically about 0.95 to 1.0 moles, per mole of fesoterodine.

The fesoterodine 2-chloro-mandalate salt is isolated in solid state form by cooling the solution of fesoterodine 2-chloro-mandalate salt and filtering and drying.

Preferably, process for preparing fesoterodine 2-chloro mandalate involves combining of the solution of fesoterodine in organic solvent with 2-chloro-mandelic acid in step-(b) is performed in a suitable order, for example, the first solution is added to the 2-chloro-mandelic acid, or alternatively, the 2-chloro-mandelic acid is added to the first solution. The addition is, for example, carried out drop wise or in one portion or in more than one portion. The addition is specifically carried out at a temperature of about 30 C to about 100° C., more specifically at about 20° C. to about 50° C., and most specifically at about 25° C. to about 40° C. under stirring. After completion of addition process, the resulting mass is stirred at a temperature of about 30° C. to about 45° C. for at least 10 minutes and specifically at a temperature of about 25° C. to about 35° C. for about 2 to 3 hours to produce a second solution.

The solution obtained after saltification reaction is optionally subjected to carbon treatment or silica gel treatment. The carbon treatment or silica gel treatment is carried out by methods known in the art, for example, by stirring the solution with finely powdered carbon or silica gel at a temperature of about 40° C. to about 70° C. for at least 30 minutes; and filtering the resulting mixture through hyflo to obtain a filtrate containing fesoterodine 2-fhloro-mandelate by removing charcoal or silica gel. Preferably, finely powdered carbon is an active carbon.

The second solution obtained in step-(b) is optionally cooled at a temperature of about −5° C. to 15° C., and specifically at a temperature of about 0° C. to about 5° C.

The isolation of fesoterodine-2-chloro-mandelate in step-(c) is carried out by forcible or spontaneous crystallization.

Spontaneous crystallization refers to crystallization without the help of an external aid such as seeding, cooling etc., and forcible crystallization refers to crystallization with the help of an external aid.

Forcible crystallization may be initiated by a method usually known in the art such as cooling, seeding, partial removal of the solvent from the solution, by adding an anti-solvent to the solution, or a combination thereof.

In one embodiment, the crystallization is carried out by cooling the solution at a temperature of about −5° C. to 10° C. for about 1 to 2 hours, and more specifically at about 5° C. to 10° C. for about 1 hour.

The substantially pure fesoterodine 2-chloro-mandelate obtained in step-(c) may be recovered by methods such as filtration, filtration under vacuum, decantation, centrifugation, or a combination thereof. In one embodiment, fesoterodine 2-chloro-mandelate is isolated by filtration employing a filtration media of, for example, a silica gel or celite.

The pure fesoterodine 2-chloro-mandelate obtained by above process may be further dried in, for example, a vacuum tray dryer, rotocon vacuum dryer, a vacuum paddle dryer or a pilot plant rota vapor, to further lower residual solvents. drying can be earned out under reduced pressure until the residual solvent content reduces to the desired amount such as an amount that is within the limits given by the ICH guidelines.

In one embodiment, the drying is carried out at atmospheric pressure or reduced pressures, such as below about 200 mm Hg, or below about 50 mm Hg, at temperatures such as about 40° C. to about 70° C. The drying can be carried out for any desired time period mat achieves the desired result, such as about 1 to 20 hours. Drying may also be carried out for shorter or longer periods of time depending on the product specifications. Temperatures and pressures will be chosen based on the volatility of the solvent being used and the foregoing should be considered as only a general guidance. Drying can be suitably carried out in a tray dryer, vacuum oven, air oven, or using a fluidized bed drier, spin flash dryer, flash dryer and the like. Drying equipment selection is well within the ordinary skill in the art.

The purity of the fesoterodine 2-chloro-mandelate obtained by the process disclosed herein is greater than about 99%, specifically greater man about 99.5%, more specifically greater than about 99.9%, and most specifically greater than about 99.95% as measured by HPLC.

The fesoterodine 2-chloro-mandelate obtained by the process disclosed herein is optionally converted into fesoterodine free base or a pharmaceutically acceptable salt thereof.

In another embodiment, there is provided a process for purification of fesoterodine, which comprises
(i) treating fesoterodine with 2-chloro-mandelic acid in one or more organic solvent,
(ii) isolating solid state form of fesoterodine with 2-chloro-mandelic acid,
(iii) treating the fesoterodine 2-chloro-mandate with base; and
(iv) obtaining pure fesoterodine;
(v) optionally, converting fesoterodine to its pharmaceutically acceptable salt.

In general, the fesoterodine 2-chloro mandelate obtained as described herein above is converted to substantially pure fesoterodine free base or a pharmaceutically acceptable salt thereof. The process involves a) contacting fesoterodine 2-chloro-mandelate with a base in a solvent to provide the pure fesoterodine, which can be optionally converted to pharmaceutically acceptable salt thereof and b) isolating highly pure fesoterodine free base or a pharmaceutically acceptable salt thereof from the reaction mass.

Exemplary solvents used in step-(a) include, but are not limited to, water, alcohols, ketones, chlorinated hydrocarbons, hydrocarbons, nitriles, esters, ethers, polar aprotic solvents, and mixtures thereof. The term solvent may also include mixtures of solvents.

In one embodiment, the solvent is selected from the group consisting of water, methanol, ethanol, n-propanol, isopropyl alcohol, n-butanol, isobutanol, tert-butanol, amyl alcohol, hexanol, acetone, methyl ethyl ketone, methyl isobutyl ketone, methyl tert-butyl ketone, acetonitrile, ethyl acetate, methyl acetate, isopropyl acetate, tert-butyl methyl acetate, ethyl formate, methylene chloride, ethylene dichloride, chloroform, carbon tetrachloride, tetrahydrofuran, dioxane, diethyl ether, diisopropyl ether, monoglyme, diglyme, n-pentane, n-hexane, n-heptane, cyclohexane, toluene, xylene, N-dimethylformamide, N,N-dimethyl acetamide, dimethylsulfoxide, and mixtures thereof; more specifically the solvent is water and methylene chloride mixture.

In one embodiment, the base used in step-(a) is selected from an organic or inorganic base.

Exemplary inorganic and organic bases include, but are not limited to, triethyl amine, dimethyl amine and tert-butyl amine, diisopropyl amine, diisopropylethyl amine.

In another embodiment, the base is an inorganic base. Exemplary inorganic bases include, but are not limited to, aqueous ammonia; hydroxides, carbonates and bicarbonates of alkali or alkaline earth metals. Specific inorganic bases are aqueous ammonia, sodium hydroxide, calcium hydroxide, magnesium hydroxide, potassium hydroxide, lithium hydroxide, sodium carbonate, potassium carbonate, lithium carbonate, sodium tert-butoxide, sodium isopropoxide and potassium tert-butoxide, and more specifically sodium hydroxide.

If the reaction in step-(a) is carried out in the presence of a base, the product obtained is pure fesoterodine base, which can be converted into a pharmaceutically acceptable acid addition salt of fesoterodine using a suitable acid in a suitable solvent.

The reaction in step-(a) is carried out at a temperature of 25° C. to the reflux temperature of the solvent used, specifically at a temperature of 0° C. to the reflux temperature of the solvent used, more specifically at a temperature of 25° C. to the reflux temperature of the solvent used, and most specifically at the reflux temperature of the solvent used.

As used herein, "reflux temperature" means the temperature at which the solvent or solvent system refluxes or boils at atmospheric pressure.

The reaction mass containing the pure fesoterodine or a pharmaceutically acceptable salt thereof may be subjected to usual work up such as washings, extractions, evaporations etc., followed by isolation from a suitable organic solvent by methods known in the art. The isolation of highly pure fesoterodine or a pharmaceutically acceptable salt thereof in step-(b) is carried out by forcible or spontaneous crystallization.

In one embodiment, the crystallization is carried out by cooling the solution at a temperature of below 30° C. for at least 30 minutes, specifically at about 30° C. to 40° C. for about 10 to 12 hours.

The pure fesoterodine or a pharmaceutically acceptable salt thereof obtained by above process is recovered and optionally further dried as described above.

Exemplary pharmaceutically acceptable salts of fesoterodine include hydrochloride, hydrobromide, sulfate, fumarate and tartarate, and more preferably fumarate.

The purity of the fesoterodine or a pharmaceutically acceptable salt thereof obtained by the process disclosed herein is of greater than about 99%, specifically greater than about 99.5%, more specifically greater than about 99.9%, and most specifically greater than about 99.95% as measured by HPLC. For example, the purity of the fesoterodine or a pharmaceutically acceptable salt thereof can be about 99% to about 99.95%, or about 99.5% to about 99.99%.

Further encompassed herein is the use of the solid state form of fesoterodine 2-chloro-mandelate for the manufacture of a pharmaceutical composition together with a pharmaceutically acceptable carrier.

Fesoterodine and its pharmaceutically acceptable salts can be prepared in high purity by using the substantially pure fesoterodine 2-chloro-mandelate obtained according to the process disclosed herein.

The invention provides one pot process for the preparation of 3-(2-(benzyloxy)-5-bromophenyl)-3-phenylpropyl methanesulfonate of formula (D). The compound of formula (D) is key intermediate for preparation of fesoterodine.

The one pot process for preparing compound of formula (D), comprises

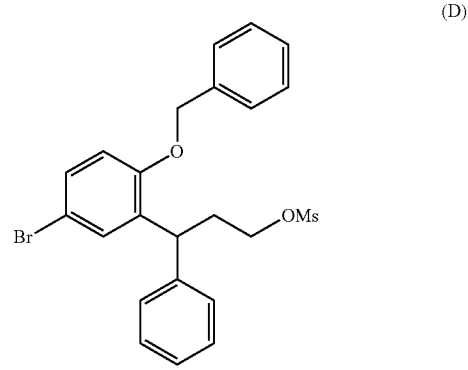 [SMILES: CS(=O)(=O)OCCC(c1ccccc1)c1cc(Br)ccc1OCc1ccccc1]

(D)

(a) reacting 6-Bromo-4-phenylchroman-2-one of formula (A) with benzyl chloride to obtain a methyl 3-(2-benzyloxy)-5-bromophenyl)-3-phenylpropanoate compound of formula (B);
(b) reducing the compound of formula (B) to obtain a 3-(2-(benzyloxy)-5-bromophenyl)-3-phenylpropan-1-ol of formula (C);
(c) activating compound of formula (C) with methane sulfonyl chloride to obtain 3-(2-(benzyloxy)-5-bromophenyl)-3-phenylpropyl methanesulfonate compound of formula (D).

The improved process for preparing 3-(2-(benzyloxy)-5-bromophenyl)-3-phenylpropyl methanesulfonate compound of formula (D) is depicted in below in Scheme-1:

The invention further provides crystalline 3-(2-(benzyloxy)-5-bromophenyl)-3-phenylpropyl methanesulfonate of formula (D)

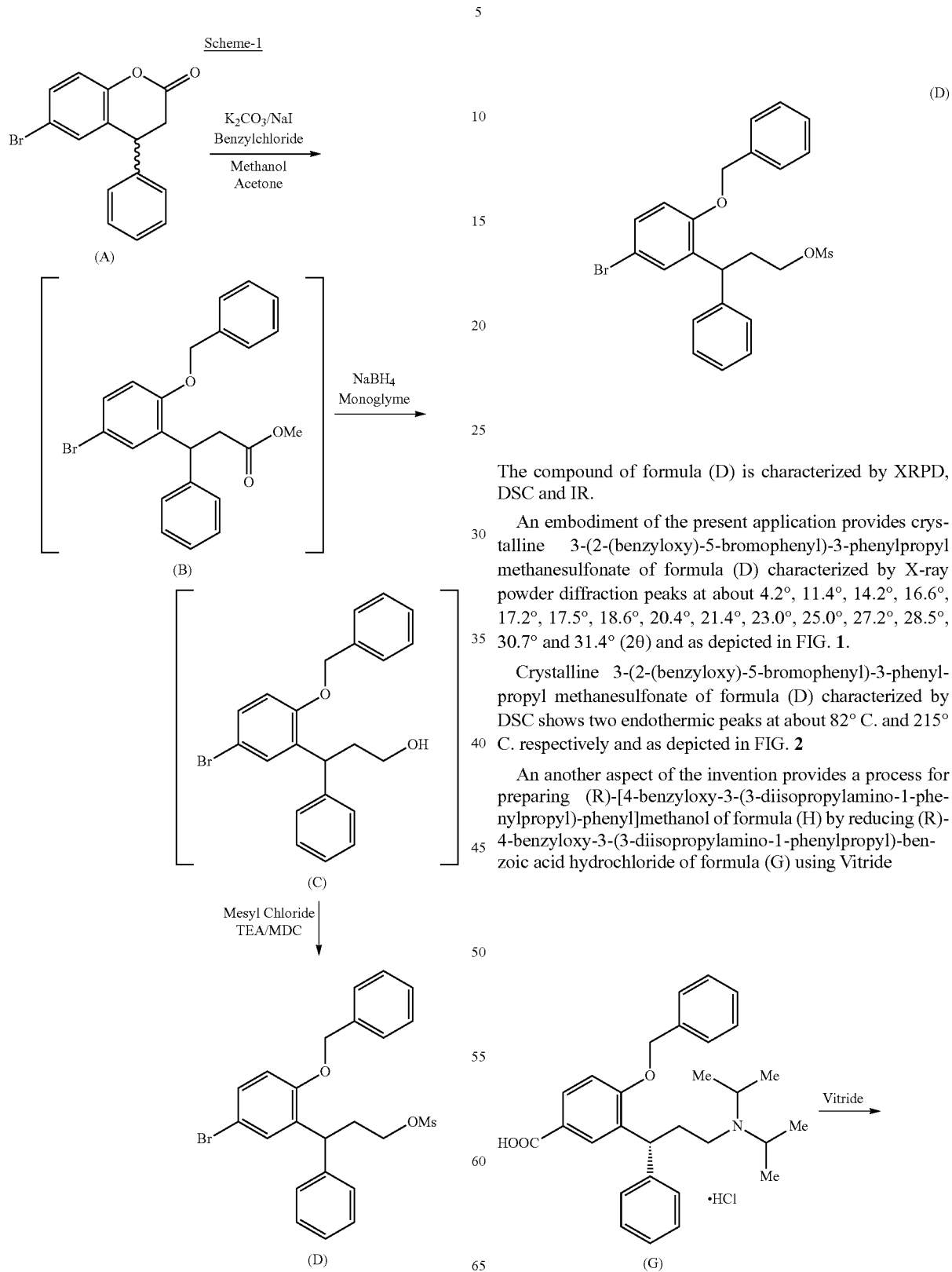

The compound of formula (D) is characterized by XRPD, DSC and IR.

An embodiment of the present application provides crystalline 3-(2-(benzyloxy)-5-bromophenyl)-3-phenylpropyl methanesulfonate of formula (D) characterized by X-ray powder diffraction peaks at about 4.2°, 11.4°, 14.2°, 16.6°, 17.2°, 17.5°, 18.6°, 20.4°, 21.4°, 23.0°, 25.0°, 27.2°, 28.5°, 30.7° and 31.4° (2θ) and as depicted in FIG. 1.

Figure 2:
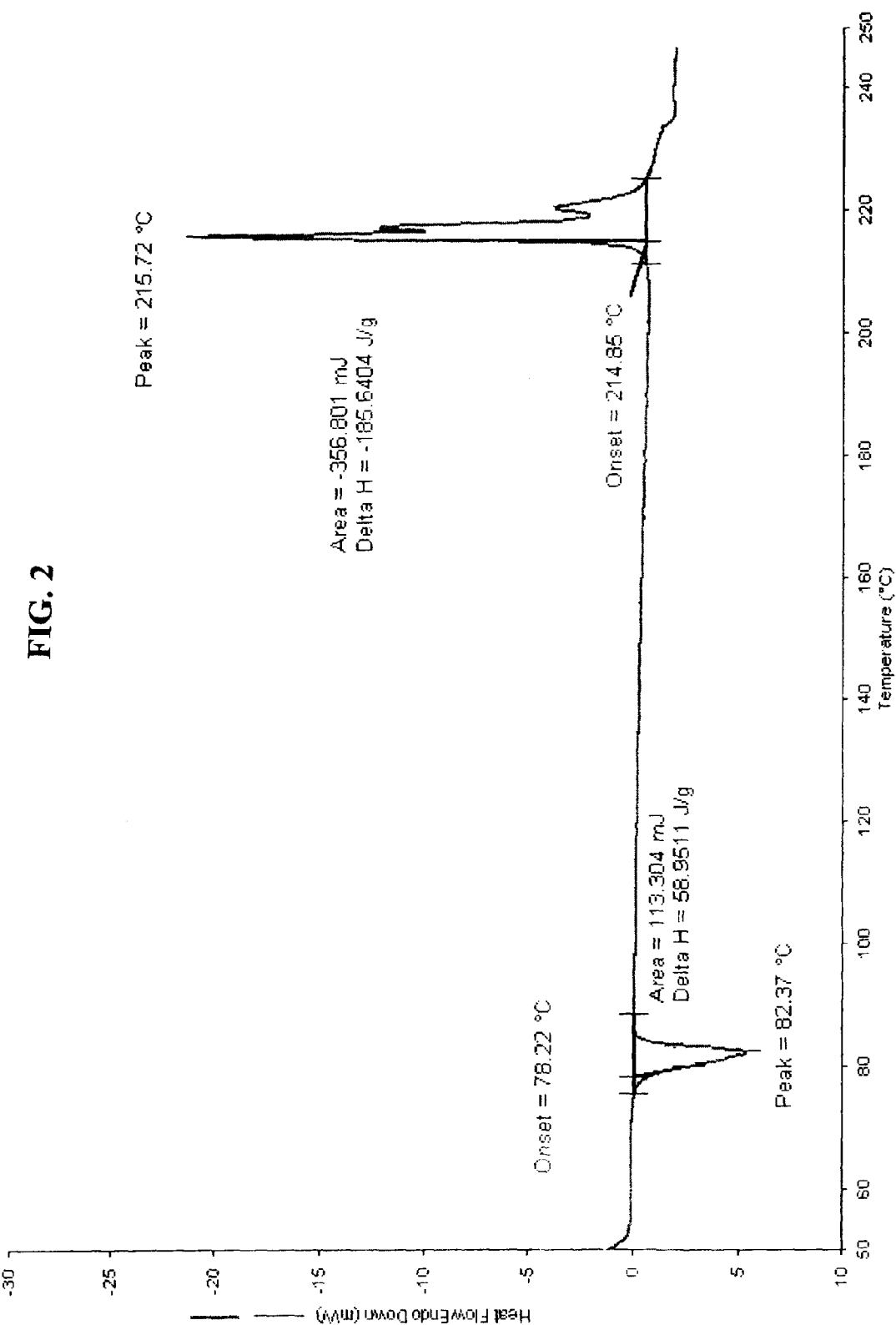

Crystalline 3-(2-(benzyloxy)-5-bromophenyl)-3-phenylpropyl methanesulfonate of formula (D) characterized by DSC shows two endothermic peaks at about 82° C. and 215° C. respectively and as depicted in FIG. 2

An another aspect of the invention provides a process for preparing (R)-[4-benzyloxy-3-(3-diisopropylamino-1-phenylpropyl)-phenyl]methanol of formula (H) by reducing (R)-4-benzyloxy-3-(3-diisopropylamino-1-phenylpropyl)-benzoic acid hydrochloride of formula (G) using Vitride

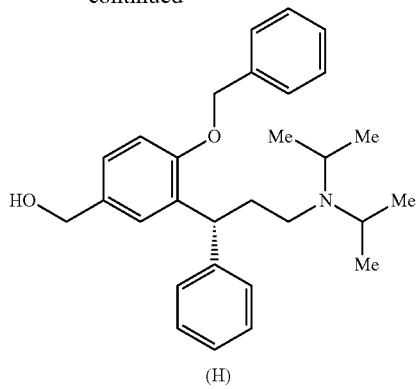

(H)

The invention provides a process for preparing (R)-[4-benzyloxy-3-(3-diisopropylamino-1-phenylpropyl)-phenyl] methanol of formula (H), comprises reducing (R)-[4-benzyloxy-3-(3-diisopropylamino-1-phenyl propyl)benzoate using Vitride.

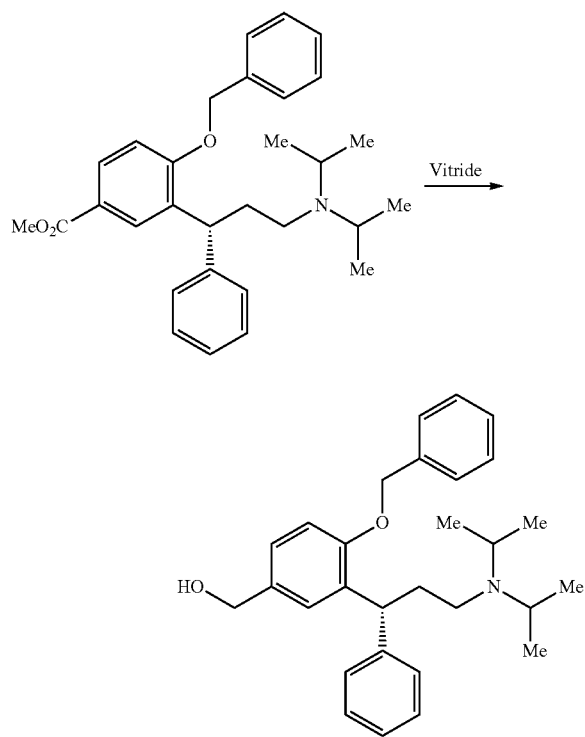

The present invention provides improved process for preparing fesoterodine and its pharmaceutically acceptable salt, which comprises (a) reacting 6-Bromo-4-phenylchroman-2-one of formula (A) with benzyl chloride to obtain a methyl 3-(2-benzyloxy)-5-bromophenyl)-3-phenylpropanoate compound of formula (B), (b) reducing the compound of formula (B) to obtain a 3-(2-(benzyloxy)-5-bromophenyl)-3-phenylpropan-1-ol of formula (C)

(c) activating compound of formula (C) with methane sulfonyl chloride to obtain 3-(2-(benzyloxy)-5-bromophenyl)-3-phenylpropyl methanesulfonate compound of formula (D), wherein compound of formula (B) and (C) are not isolated (d) reacting compound of formula (D) with diisopropylamine under neat condition or in presence of solvent to obtain 3-(2-(benzyloxy)-5-bromophenyl)-N,N-diisopropyl-3-phenylpropan-1-amine of formula (E);

(e) resolving 3-(2-(benzyloxy)-5-bromophenyl)-N,N-diisopropyl-3-phenylpropan-1-amine of formula (E) with a suitable optically active acid to obtain (R)—N,N-Diisopropyl-3-(2-benzyloxy-5-bromophenyl)-3-phenylpropyl amine of formula (F);

(f) reacting (R)—N,N-Diisopropyl-3-(2-benzyloxy-5-bromophenyl)-3-phenylpropyl amine of formula (F) with ethyl halide and Magnesium in presence of solid carbon dioxide to obtain (R)-4-benzyloxy-3-(3-diisopropylamino-1-phenylpropyl)-benzoic acid hydrochloride of formula (G);

(g) reacting (R)-4-benzyloxy-3-(3-diisopropylamino-1-phenylpropyl)-benzoic acid hydro chloride of formula (G) with Vitride in presence of organic solvent to obtain (R)-[4-benzyloxy-3-(3-diisopropylamino-1-phenylpropyl)-phenyl]-methanol of formula (H);

(h) de-protecting (R)-[4-benzyloxy-3-(3-diisopropylamino-1-phenylpropyl)-phenyl]-methanol of formula (H) with reducing agent to obtain (R)-2-(3-diisopropylamino-1-phenylpropyl)-4-hydroxy methyl phenol of formula (I);

(i) condensing (R)-2-(3-diisopropylamino-1-phenylpropyl)-4-hydroxy methyl phenol of formula (I) with isobutyryl halide in a suitable solvent, optionally in the presence of base to obtain fesoterodine of formula (J);

(j) optionally, purifying fesoterodine by 2-chloro-mandelate salt formation and;

(k) optionally, converting fesoterodine into a pharmaceutically acceptable acid addition salt.

The improved process of the invention produces fesoterodine fumarate containing less than about 0.1% of the individual impurities.

In an aspect the present application provides a process for the preparation of fesoterodine or its pharmaceutically acceptable salt, preferably fumarate salt, the process comprises:

(a) reacting (R)-4-(benzyloxy)-3-(3-(diisopropylamino)-1-phenylpropyl)benzoic acid hydrochloride of formula (G) with Vitride in suitable solvent to obtain (R)-(4-(benzyloxy)-3-(3-(diisopropylamino)-1-phenylpropyl)phenyl) methanol of formula (H);

(b) de-protecting (R)-(4-(benzyloxy)-3-(3-(diisopropylamino)-1-phenylpropyl)phenyl)methanol of formula (H) to give (R)-2-(3-(diisopropylamino)-1-phenylpropyl)-4-(hydroxy methyl)phenol of formula (I);

(c) condensing (R)-2-(3-(diisopropylamino)-1-phenylpropyl)-4-(hydroxymethyl)phenol of formula (I) with isobutyryl chloride in a suitable solvent, optionally in the presence of base to produce Fesoterodine base of formula (J);

(d) converting Fesoterodine of formula (J) in to a pharmaceutically acceptable acid addition salt.

Preferably, the process for preparation of Fesoterodine fumarate compound of formula (1) shown in below Scheme-2:

Scheme-2

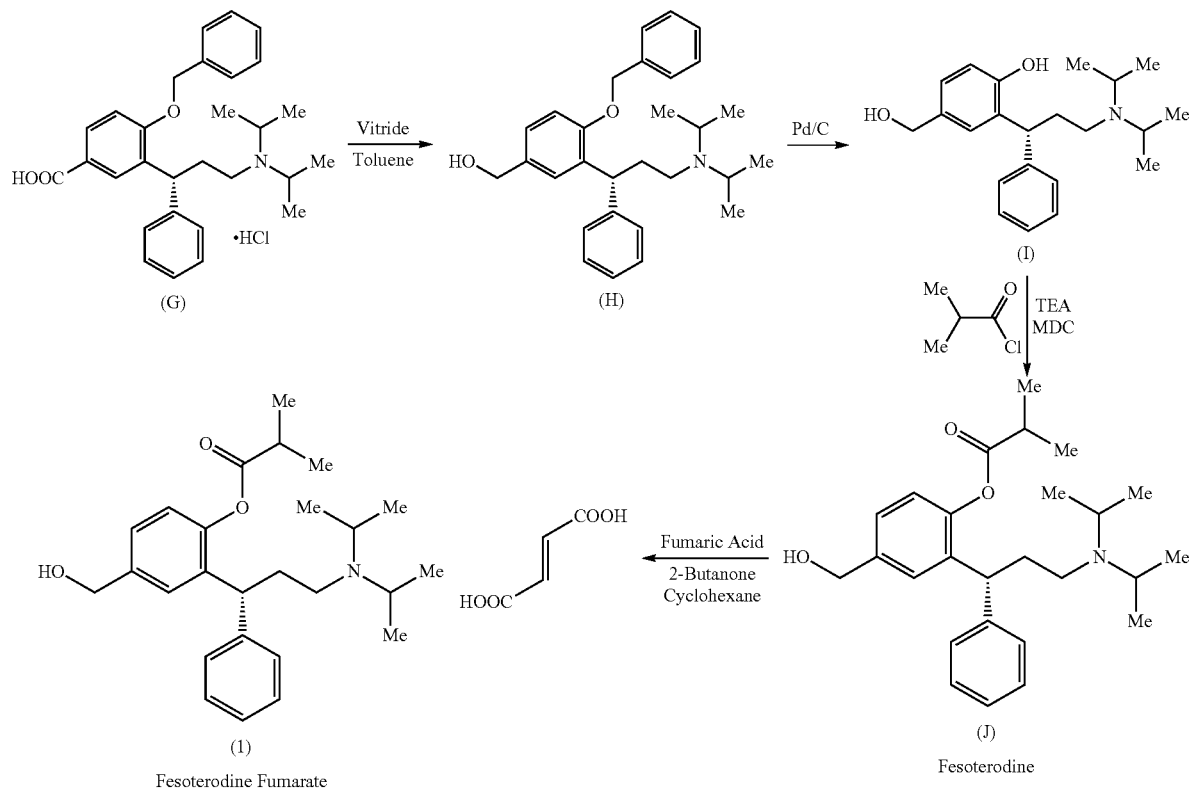

(1) Fesoterodine Fumarate (J) Fesoterodine

The invention provides a process for preparing pure (R)-4-(benzyloxy)-3-(3-(diisopropylamino)-1-phenylpropyl) benzoic acid hydrochloride of formula (G), from 3-(2-(benzyloxy)-5-bromophenyl)-3-phenylpropyl methanesulfonate of formula (D), which avoids the formation of Dimer impurity. Further the pure compound of formula (G), avoids the side reaction and byproduct formation. Further, the inventors have also found that the isolation of Fesoterodine by using acetone and water for the reaction with isobutyryl chloride in the presence of inorganic base unlike the organic bases used in the art provides better yield and purity. This significantly improves the process economics and commercial viability.

In general embodiment, 6-Bromo-4-phenylchroman-2-one of formula (A) is reacted with benzyl chloride in the presence of sodium iodide and suitable base such as potassium carbonate for in-situ formation of Methyl 3-(2-benzyloxy)-5-bromophenyl)-3-phenylpropanoate of formula (B); which is reducing with a reducing agent such as sodium borohydride in the presence of Lewis acid such as aluminium chloride with monoglyme for in-situ formation of 3-(2-(benzyloxy)-5-bromophenyl)-3-phenylpropan-1-ol of formula (C); reacting compound of formula (C) with mesyl chloride in presence of aliphatic organic base such as triethyl amine and organic solvent such as methylene dichloride to isolate 3-(2-(benzyloxy)-5-bromophenyl)-3-phenylpropyl methanesulfonate of formula (D).

3-(2-(benzyloxy)-5-bromophenyl)-3-phenylpropyl methanesulfonate of formula (D) is converted to N,N-Diisopropyl-3-(2-benzyloxy-5-bromophenyl)-3-phenylpropylamine of formula (E) by reacting with diisopropylamine both in neat reaction condition or in presence of solvent such as acetonitrile, water etc, preferably water.

N,N-Diisopropyl-3-(2-benzyloxy-5-bromophenyl)-3-phenylpropylamine of formula (E) is resolved by using diaroyl-tartaric acid such as (−)-di-p-toluoyl-L-tartaric acid, (+)-di-p-toluoyl-D-tartaric acid, (−)-dibenzoyl-L-tartaric acid, (+)-dibenzoyl-D-tartatic acid, and hydrates, preferably (−)-di-p-toluoyl-L-tartaric acid.

The organic solvent for resolution of N,N-Diisopropyl-3-(2-benzyloxy-5-bromophenyl)-3-phenylpropylamine of formula (E) is selected from water, acetone, acetonitrile, $C_1$-$C_4$ alcohols, halogenated solvents, toluene, 1,4-dioxan etc; preferably isopropyl alcohol.

(R)—N,N-Diisopropyl-3-(2-benzyloxy-5-bromophenyl)-3-Phenylpropylamine compound of formula (F) is reacted with ethyl bromide and magnesium in presence of solid or gaseous carbon dioxide, wherein the preferred solvent is THF to isolate (R)-4-benzyloxy-3-(3-diisopropylamino-1-phenylpropyl)-benzoic acid hydrochloride of formula (G).

(R)-4-benzyloxy-3-(3-diisopropylamino-1-phenylpropyl)-benzoic acid hydrochloride of formula (G) is reacted with Vitride (Sodium dihydrobis (2-methoxyethoxy)aluminate) in the presence of preferred organic solvent toluene by which directly (R)-[4-benzyloxy-3-(3-diisopropylamino-1-phenylpropyl)-phenyl]-methanol of formula (H) is obtained.

(R)-[4-benzyloxy-3-(3-diisopropylamino-1-phenylpropyl)-phenyl]-methanol of formula (H) is reduced by using Pd/C in the presence of alcoholic solvents, preferably methanol to obtain (R)-2-(3-diisopropylamino-1-phenylpropyl)-4-hydroxy methyl phenol of formula (I) which is recrystallized with mixture of ethyl acetate and hexane.

(R)-2-(3-diisopropylamino-1-phenylpropyl)-4-hydroxy methyl phenol of formula (I) is reacted with isobutyryl chloride in presence of base in one or more organic solvent such as acetone, water, halogenated solvent, preferably in MDC or mixture of acetone-water.

The reaction involves presence of base which can be selected from organic and inorganic base like triethyl amine, diisopropyl amine, diisopropyl ethyl amine, sodium carbonate, potassium carbonate etc, the preferred organic base is triethyl amine or diisopropyl amine; the preferred inorganic base is sodium carbonate.

The fesoterodine of formula (J) is converted into fumarate salt by reacting with fumaric acid in the presence of solvent such as 2-butanone and cyclohexane to obtain pure fesoterodine fumarate.

"Substantially pure fesoterodine fumarate" refers fesoterodine fumarate substantially free from any of the impurities FFA-Diol (i), FFA-Diester (a) (ii), FFA-Diester (b) (iii), FFA-Dehydroxy (iv), FFA-(S)(−)-isomer (v), FFA-Methanol analogue (vi), FFA-Isopropylamine analogue (vii), FFA-Dimer (viii) and FFA-Amide (ix) respectively. The impurities (i), (ii), (iii), (iv), (v), (vi), (vii), (viii) (ix) individually are less than about 0.15% by area percentage of HPLC, preferably less than about 0.1%, more preferably less than about 0.07% by area percentage of HPLC.

An another aspect of the present application provides a process for determining purity of fesoterodine fumarate (1) comprising carrying out UPLC or HPLC or TLC with any of the following impurities
i)  (R)-2-(3-(Diisopropylamino)-1-phenylpropyl)-4-(hydroxymethyl)phenol i.e. FFA-Diol
ii) (R)-Methyl 3-(3-(diisopropylamino)-1-phenylpropyl)-4-(isobutyryloxy)benzoate i.e. FFA-Diester (a)
iii) (R)-3-(3-(Diisopropylamino)-1-phenylpropyl)-4-(isobutyryloxy)benzyl isobutyrate i.e. FFA-Diester (b).
iv) (R)-2-(3-(diisopropylamino)-1-phenylpropyl)-4-methylphenyl isobutyrate i.e. FFA-Dehydroxy
v) (S)(−)-Fesoterodine i.e. FFA-(S)(−)-isomer
vi) (R)-(4-(benzyloxy)-3-(3-(diisopropylamino)-1-phenylpropyl)phenyl)methanol i.e. FFA-Methanol analogue
vii) (R)-4-(hydroxymethyl)-2-(3-(isopropylamino)-1-phenylpropyl)phenylisobutyrate i.e. FFA-Isopropylamine analogue
viii) 4-(hydroxymethyl)-2-((R)-3-(((S)-3-(5-(hydroxymethyl)-2-(isobutyryloxy)phenyl)-3-phenylpropyl)(isopropyl)amino)-1-phenylpropyl)phenyl isobutyrate i.e. FFA-Dimer
ix) (R)-4-(hydroxymethyl)-2-(3-(N-isopropylisobutyramido)-1-phenylpropyl)phenyl iso-butyrate i.e. FFA-Amide; as a reference markers.

The invention further provides a method to determine the presence of any one of the impurities selected from FFA-Diol or FFA-Diester(a) or FFA-Diester(b) or FFA-Dehydroxy or FFA-(S)(−)-isomer or FFA-Methanol analogue or FFA-Isopropylamine analogue or FFA-Dimer or FFA-Amide in fesoterodine fumarate (I) comprising:
(a) combining a fesoterodine fumarate (1) sample with a buffer to obtain a solution;
(b) injecting the obtained solution into a 150 mm×4.6 mm, 5 μm) Kromasil C-18 (or similar) column,
(c) gradient eluting the sample from the column at about 60 min using a mixture of Buffer (referred to as eluent A) and acetonitrile (referred to as eluent B); and
(d) measuring the content of FFA-Diol or FFA-Diester(a) or FFA-Diester(b) or FFA-Dehydroxy or FFA-(S)(−)-isomer or FFA-Methanol analogue or FFA-Isopropylamine analogue or FFA-Dimer or FFA-Amide in the relevant sample with a UV detector (preferably at a 318 nm wavelength).

In yet another general aspect, there is provided a process for preparing fesoterodine fumarate (I) containing less than about 0.1% of one or more of FFA-Diol, FFA-Diester (a), FFA-Diester (b), FFA-Dehydroxy and FFA-(S)(−)-isomer comprising:

a) obtaining a sample of fesoterodine fumarate technical;
b) measuring the amount of one or more impurities selected from the group consisting of FFA-Diol, FFA-Diester(a), FFA-Diester(b), FFA-Dehydroxy and FFA-(S)(−)-isomer in the sample of fesoterodine fumarate technical;
c) selecting a sample of fesoterodine fumarate technical in which the amount of one or more of the measured impurities is more than about 0.1%; and
d) purifying fesoterodine fumarate technical with suitable solvent to obtain fesoterodine fumarate.

In yet another general aspect, there is provided a process for preparing substantially pure fesoterodine fumarate (1) containing less than about 0.1% of one or more of impurity, FFA-Methanol analogue, FFA-Isopropylamine analogue, FFA-Dimer or FFA-Amide; comprising:

a) obtaining a sample of fesoterodine base;
b) measuring the amount of one or more impurities selected from the group consisting of FFA-Methanol analogue, FFA-Isopropylamine analogue, FFA-Dimer and FFA-Amide in the sample of Fesoterodine base;
c) selecting a sample of fesoterodine base in which the amount of one or more of the measured impurities is less than about 0.1%; and
d) converting said fesoterodine base to in to substantially pure fesoterodine fumarate (1).

The chemical structures of impurities FFA-Diol, FFA-Diester (a), FFA-Diester (b), FFA-Dehydroxy, FFA-(S)(−)-isomer, FFA-Methanol analogue, FFA-Isopropylamine analogue, FFA-Dimer and FFA-Amide are:

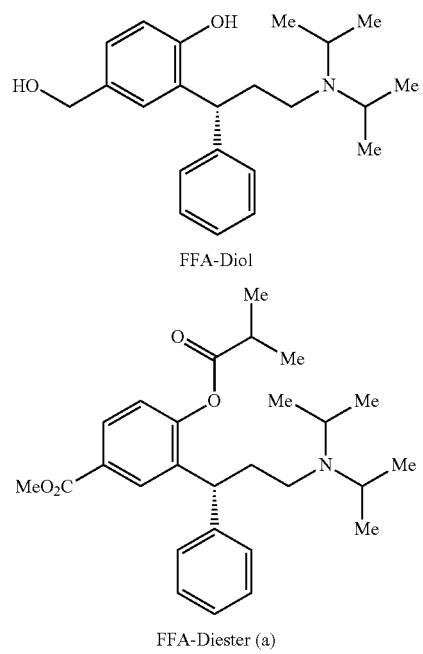

FFA-Diol

FFA-Diester (a)

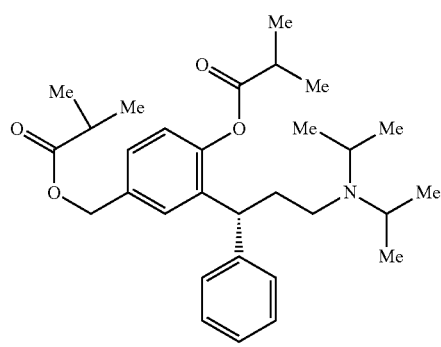

FFA-Diester (b)

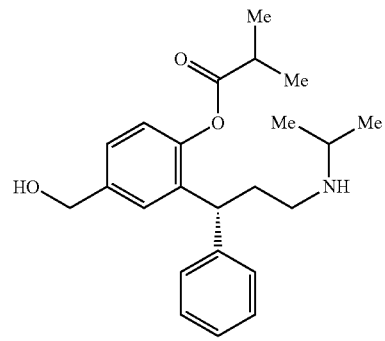

FFA-Isopropylamine analogue

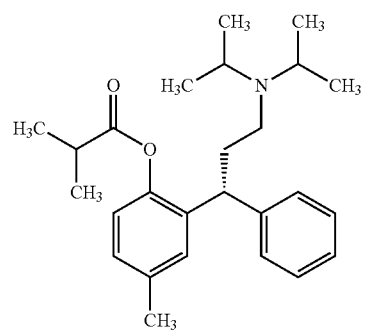

FFA-Dehydroxy

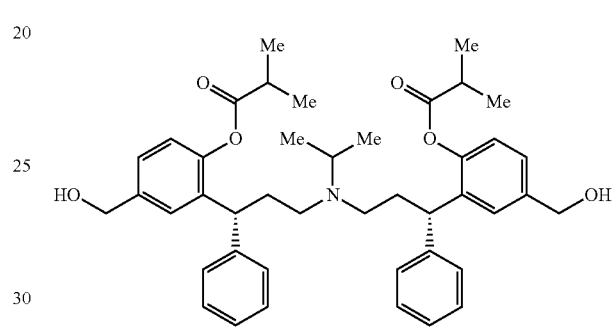

FFA-Dimer

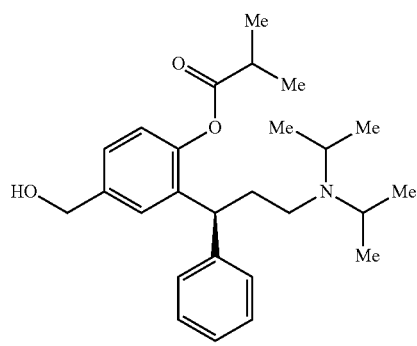

FFA-(S)(-)-isomer

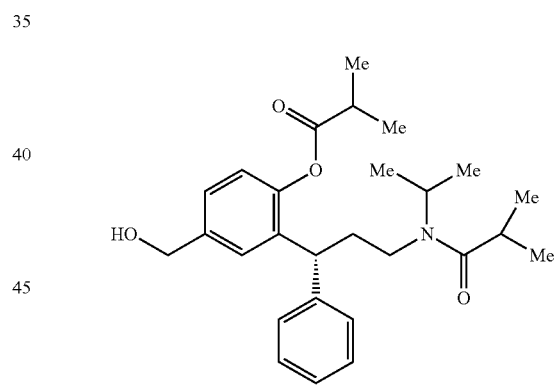

FAA-Amide

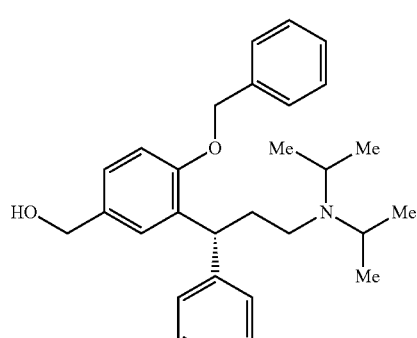

FFA-Methanol analogue

Figure 3:
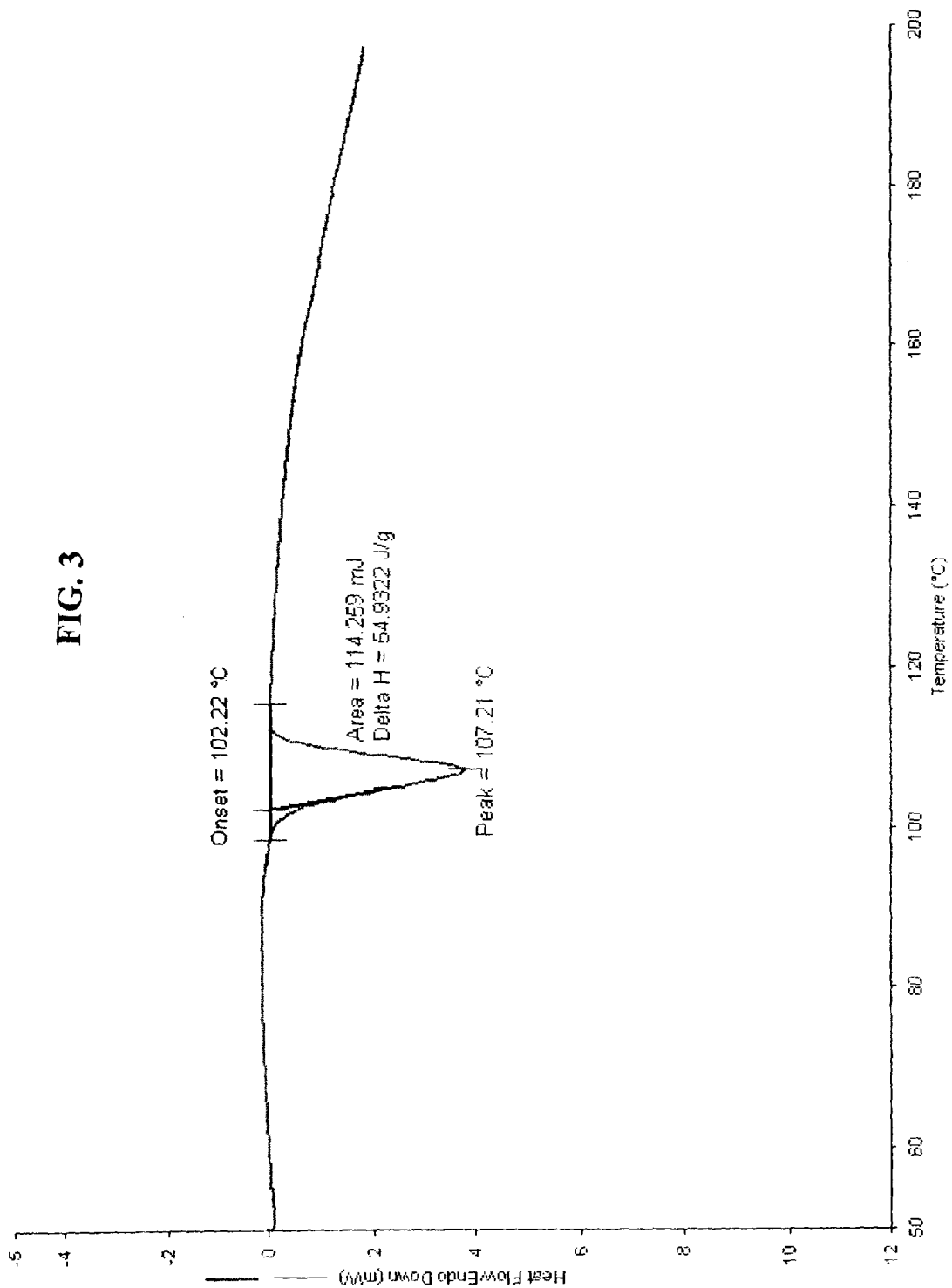

Another embodiment of the present application provides pure fesoterodine Fumarate (1) characterized by DSC having an endothermic peak at about 107° C. and as depicted in FIG. 3

Figure 4:
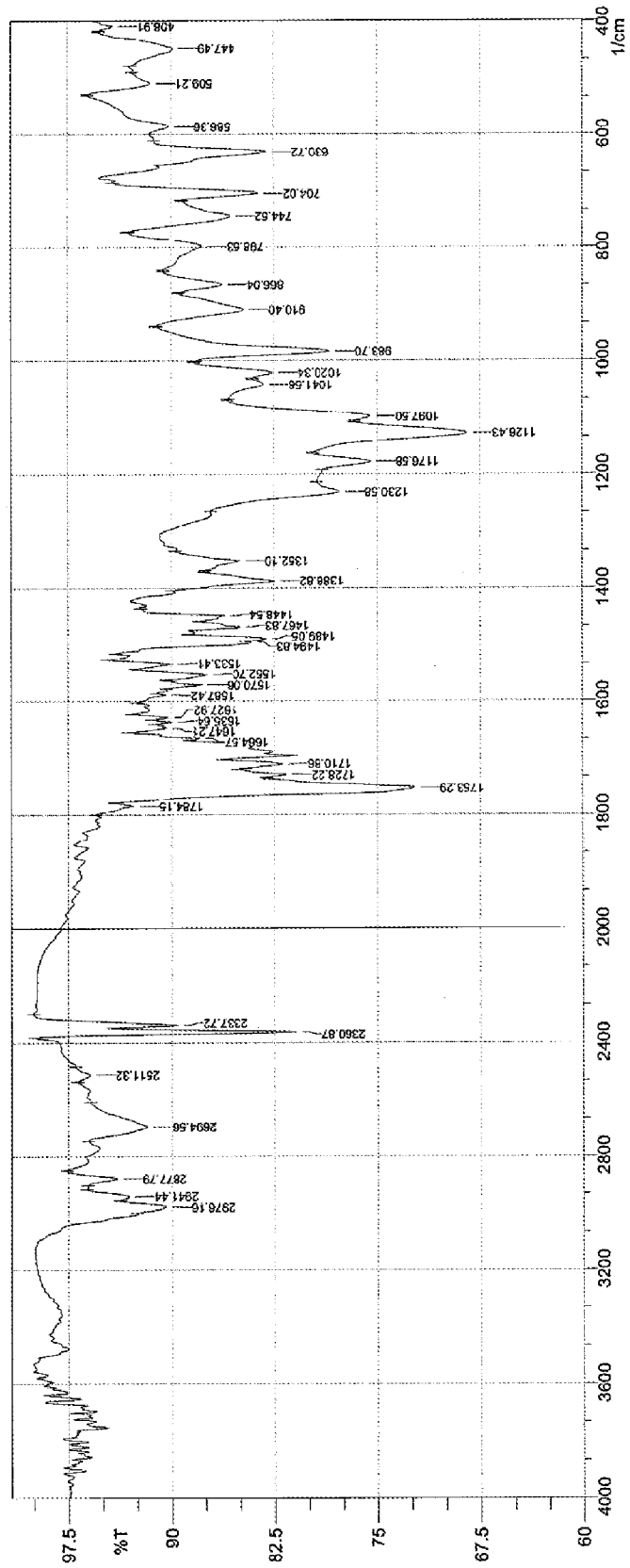

Another embodiment of the present application provides pure fesoterodine fumarate (1) characterized by IR peaks at about 3380, 2978, 2939, 2878, 2692, 2514, 1756, 1702, 1680, 1618, 1496, 1468, 1226, 1040, 1019 and 806 cm$^{-1}$ and as depicted in FIG. 4.

In general aspect, there is provided a highly pure Fesoterodine fumarate of formula (1)

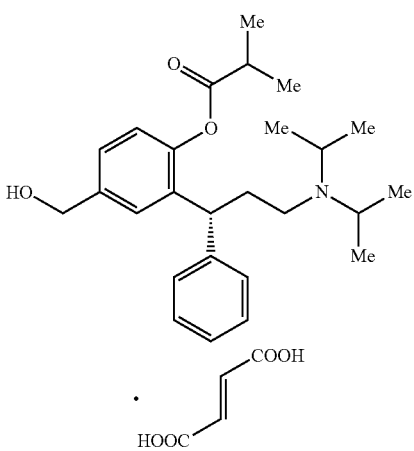

substantially free of impurity X at RRT 1.37. The 'impurity X' at RRT 1.37 is having molecular mass 409.

As used herein, "fesoterodine fumarate substantially free of impurity X at RRT 1.37" refers to fesoterodine fumarate having a purity of about 99% to about 99.99% and further comprising impurity X at RRT 1.37 in an amount of less than about 0.15% as measured by HPLC.

In another aspect, provided herein is Fesoterodine Fumarate that comprises impurity X in an amount of about 0.01% to about 0.15%, specifically in an amount of about 0.01% to about 0.03% as measured by HPLC.

It is observed in the development of pharmaceutical substance that certain impurities generated during preparation of intermediate and carry forward in the product in subsequent step and participates in reaction like manner. The carry forward impurities generated are difficult to remove in final product.

Surprisingly, it is found by the inventors that the impurity X observed at RRT 1.37 in fesoterodine fumarate is carry forward impurity. The reciprocating impurity is observed at RRT 1.3 having molecular mass of 339 during the formation of compound of below formula (I) i.e. (R)-2-(3-(Diisopropylamino)-1-phenylpropyl)-4-(hydroxymethyl)phenol.

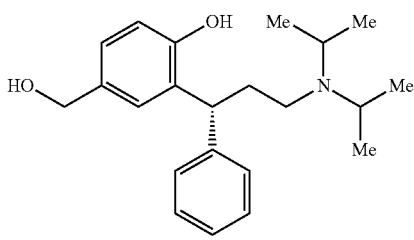

It has been observed that compound of formula (I) contains 0.15% to 2% or more of impurity X at RRT about 1.3 having molecular mass 339 as determined by HPLC.

The invention further provides a process for preparing fesoterodine fumarate substantially of impurity X at RRT 1.37 by obtaining pure compound of formula (I). The invention provides process for preparing pure (R)-2-(3-(Diisopropylamino)-1-phenylpropyl)-4-(hydroxymethyl)phenol compound of formula (I) comprises treating compound of formula (I) with a reducing agent in a suitable solvent, and then isolating pure compound of formula (I).

According to another aspect, the process for preparing highly pure compound of formula (I) being substantially free of impurity X at RRT about 1.3 having molecular mass 339, comprising:
a) adding a reducing agent to the solution of compound of formula (I);
b) heating the reaction mass;
c) cooling the reaction mass;
d) isolating highly pure compound of formula (I).

The reducing agent used in step (a) includes metal hydrides such as sodium borohydride, sodium cyanoborohydride, sodium bis(2-methoxyethoxy)aluminium hydride, lithium borohydride, potassium borohydride, and combinations comprising one or more of the foregoing reducing agents. A specific reducing agent is sodium borohydride.

The reaction mass is heated in step (c) at 50° C. to 80° C., preferably at 65° C. to 70° C. The reaction is maintained for 30 to 40 minutes at the preferable heating temperature.

The reaction mass is cooled in step (c) at 20° C. to 40° C., preferably 25° C. to 35° C. The reaction is maintained for about 2 hours at the preferable cooling temperature.

The reaction mass is further cooled to 0° C. to 5° C. in step (c) and maintained for about 30 to 40 minutes for obtaining the highly pure compound of formula (I).

The highly pure compound of formula (I) is isolated in step (d) by filtration, filtration under vacuum, decantation, centrifugation, or a combination thereof.

Substantially pure compound of formula (I) free of impurity X at RRT 1.3 refers to compound of formula (I) has a purity of about 99% to about 99.99% and further comprising impurity X at RRT 1.3 in an amount of less than about 0.15% as measured by HPLC. Specifically, compound of formula (I) as disclosed herein contains less than about 0.1%, more specifically less than about 0.06%, still more specifically less than about 0.03% of impurity X, and most specifically is essentially free of impurity X.

In another aspect of the present invention substantially pure compound of formula (I) free of impurity X at RRT 1.3 is further converted to highly pure Fesoterodine Fumarate.

The process for preparing Fesoterodine or its pharmaceutically acceptable salt from substantially pure compound of formula (I) free of impurity X at RRT 1.37 comprises;
(a) treating (R)-2-(3-diisopropylamino-1-phenylpropyl)-4-hydroxy methyl phenol of formula (I) with reducing agent to obtain pure compound of formula (I),
(b) condensing pure compound of formula (I) with isobutyryl halide in one or more solvent, optionally in presence of base to obtain fesoterodine substantially free of impurity X
(c) optionally, converting fesoterodine substantially free of impurity X to pharmaceutically acceptable salts.

The isobutyrly halide used in step (b) involves isobutyryl chloride, isobutyryl bromide.

In general, (R)-2-(3-diisopropylamino-1-phenylpropyl)-4-hydroxy methyl phenol i.e. compound of formula (I) is reacted with isobutyryl chloride in step (b) in presence of organic solvent such as acetone, water, halogenated solvent, prefrebly in MDC or mixture of acetone-water.

The reaction involves presence of base in step (b), which can be selected from both organic and inorganic base such as triethyl amine, diisopropyl amine, diisopropyl ethyl amine, sodium carbonate, potassium carbonate etc, the preferred organic base is triethyl amine or diisopropyl amine and the preferred inorganic base is sodium carbonate to obtain substantially pure Fesoterodine.

Substantially pure Fesoterodine is converted into fumarate salt by reacting with fumaric acid in the presence of solvent such as 2-butanone and cyclohexane to obtain highly pure Fesoterodine Fumarate substantially free of impurity X at RRT about 1.37.

Fesoterodine fumarate exhibits substantial degradation in a humid environment and at increased temperature or under the stress condition, when prepared as per the conventional process. It is believed that hydrolyzation and oxidation are among the major mechanisms resulting in degradation.

It has been found, surprisingly, that fesoterodine fumarate with higher particle size significantly slow down the degradation of fesoterodine under stress conditions. According to another aspect, provided herein is fesoterodine fumarate having a 90 volume-percent of the particles (D90) with a size of about 250 microns to about 1200 microns.

Fesoterodine fumate having a large particle size, disclosed herein, can be filtered and dried easily.

It is unexpected found by inventors that large particle size of fesoterodine fumarate allows minimizes degradation under stress condition and provides stable fesoterodine fumarate.

According to another aspect, there is provided a process for the preparation of stable fesoterodine fumarate having a 90 volume-percent of the particles ($D_{90}$) with a size of about 250 microns to about 1200 microns, comprising:
  a) providing a solution of substantially pure fesoterodine in a one or more first solvent
  b) treating the said solution with fumaric acid at about 25° C. to 100° C.
  c) optionally, adding second solvent to the solution
  d) adding seed of fesoterodine fumarate
  e) gradual cooling to crystallize fesoterodine fumarate
  f) isolating stable fesoteoridne fumarate.

In general first solvent used in step-(a) includes, but are not limited to, $C_1$ to $C_8$ straight or branched chain alcohol, ketones, esters and the like. The exemplary solvent is methanol, ethanol, propanol, isopropanol, n-butanol, tert-butanol, amyl alcohol, isoamyl alcohol, hexanol, ethyl acetate, isopropyl acetate, n-butyl acetate, tert-butyl acetate, acetone, methyl ethyl ketone, methyl isobutyl ketone.

In one embodiment, the substantially pure fesoterodine is dissolved in the first solvent at a temperature of about 10° C. to the reflux temperature of the first solvent used.

In another embodiment, the solution in step-(a) is prepared by dissolving fesoterodine in an ketonic solvent.

In further embodiment, the solution in step-(a) is treated with fumaric acid at temp at a temperature of about 25° C. to 100° C. to form fumarate salt.

Optionally, the second solvent is added to the solution obtained in step (b). The second solvent includes hydrocarbon solvent selected from n-pentane, n-hexane, n-heptane, cyclohexane, toluene, xylene and the like.

The gradual cooling of the solution in step-(e) is performed, for example, by slowly cooling the solution initially to a temperature of below about 25° C., specifically at a temperature of about 15° C. to about 5° C. for at least 30 minutes, while slow stirring or without stirring; maintaining the resulting solution at the same temperature for at least 30 minutes, specifically from about 30 minutes to about 3 hours; and further cooling the resulting solution to a temperature of below about 5° C.

The fesoterodine fumarate obtained in step-(f) is recovered by techniques such as filtration, filtration under vacuum, decantation, and centrifugation, or a combination thereof. In one embodiment, the rasagiline mesylate solid can be recovered by filtration employing a filtration media of, for example, a silica gel or celite.

The process of the present invention can be performed on an industrial scale.

The pure fesoterodine fumarate obtained by the process has a $D_{90}$ particle size of about 250 microns to about 1200 microns.

Particle Size Distribution (PSD)" is determined by laser diffraction in a Malvern Master Sizer by using known method.

An embodiment of the present invention provides pharmaceutical compositions comprising a therapeutically effective amount of crystalline fesoterodine fumarate substantially free from impurities, and one or more pharmaceutically acceptable carriers, excipients or diluents.

An embodiment of the present invention provides a method of treating symptoms of overactive bladder (OAB), the method comprising providing a dosage form that includes crystalline Fesoterodine Fumarate substantially free from impurities.

The present invention is further illustrated by the following examples which are provided merely to be exemplary of the invention and do not limit the scope of the invention. Certain modification and equivalents will be apparent to those skilled in the art and are intended to be included within the scope of the present invention.

EXAMPLES

Example 1

Preparation of 3-(2-(benzyloxy)-5-bromophenyl)-3-phenylpropyl methanesulfonate (D)

23.8 g of conc. sulphuric acid was slowly added at 25° C. to 35° C. to a mixture of 100 g p-Bromo phenol and 81.4 g cinnamic acid. The reaction mass was heated at 120° C. to 125° C. for about 4 hours. The reaction mass was cooled to 80° C. to 82° C. and 300 ml of toluene was added followed by the addition of 200 ml water. The reaction mass was cooled to 35° C. to 40° C. The layers were separated and further toluene layer was taken and distilled out completely under vacuum below 60° C. Further, 150 ml IPA was added at 25° C. to 35° C. and cooled to 0° C. to 5° C. and washed with 2×25 ml of IPA to afford the title compound as 6-Bromo-4-phenylchroman-2-one of formula (A).

To 100 g 6-Bromo-4-phenylchroman-2-one of formula (A), 400 ml of acetone and 400 ml methanol were added, followed by the addition of 24.7 g sodium iodide, 50.1 g benzyl chloride and 55.2 g of potassium carbonate at 25° C. to 35° C. and heated at 55° C. to 60° C. and maintained for two hours. The residue was cooled up to 20° C. to 25° C. followed by the addition of 500 ml of methylene dichloride (MDC) and 1000 ml of R.O. water and stirred for 30 minutes at 25° C. to 35° C. The layers were separated and to the MDC layer 1000 ml of water was added and stirred for 30 minutes. MDC was distilled out under vacuum below 50° C. and co-distilled by 2×50 ml Toluene at 60° C. to afford the residue of methyl 3-(2-benzyloxy)-5-bromophenyl)-3-phenylpropanoate of formula (B), which was directly taken for the next step.

Further, to the residue of methyl 3-(2-benzyloxy)-5-bromophenyl)-3-phenylpropanoate of formula (B), 400 ml of monoglyme is added at 25° C. to 35° C. and cooled to 0° C. to 10° C. Slowly 14.9 g sodium borohydride was added and potion wise 21.99 g Aluminum chloride was added within 2 hours. Temperature was raised to 5° C. to 10° C. and stirred for 1.5 hours. The reaction mass was cooled to 0° C. to 5° C. followed by slow addition of 500 ml of 20% hydrochloric solution, 500 ml of MDC and 70 ml f R.O. Water. The reaction mass was heated to 25° C. to 35° C. and maintained for 30 minutes. Layers were separated and to the Aq. Layer 200 ml of MDC was added and stirred and finally MDC was distilled completely under vacuum to afford 3-(2-(benzyloxy)-5-bromophenyl)-3-phenylpropan-1-ol of formula (C), which was directly taken for the next step.

500 ml MDC was added in the residue of 3-(2-(benzyloxy)-5-bromophenyl)-3-phenylpropan-1-ol of formula (C) followed by the addition of 50.1 g triethyl amine at 25° C. to 35° C. Reaction mass was cooled to 20° C. to 25° C. followed by the addition of 48.96 g methane sulphonyl chloride. Temperature was raised to 25° C. to 30° C. and maintained for 30 minutes. Further, 300 ml water was added and reaction mass was cooled to 0° C. to 5° C. and pH adjusted to 2 to 3 using 20% hydrochloric acid solution. The reaction temperature was raised to 25° C. to 35° C. and stirred for 30 minutes. The layers were separated and to the MDC layer added 5 g of activated charcoal and stirred for 30 minutes. MDC was distilled out under vacuum below 50° C. and co-distil by 2×50 ml methanol. The residue was treated with 300 ml methanol and heated up to 60° C. to 65° C. and maintained for 1 hour. Further, reaction mass was cooled to 25° C. to 35° C. and further cooled to 0° C. to 5° C. Finally the product was washed with 2×50 ml chilled methanol and dried in hot air oven at 55° C. to 60° C. to afford the title compound 3-(2-(benzyloxy)-5-bromophenyl)-3-phenylpropyl methanesulfonate of formula (D).

Example 2

Preparation of (R)—N,N-Diisopropyl-3-(2-benzyloxy-5-bromophenyl)-3-phenylpropyl amine (F)

100 g 3-(2-(benzyloxy)-5-bromophenyl)-3-phenylpropyl methanesulfonate of formula (D) and 400 ml diisopropyl amine in charged in 2 L SSR autoclave cell at 25° C. to 35° C.

Reaction temperature was raised to 110° C. to 112° C. and maintained for 30 to 60 hours at 95° C. to 100° C. The reaction mass was cooled to 60° C. to 65° C. and further cooled to 20° C. to 25° C. The reaction mass was transferred into 1 L plastic beaker and wash the stirrer with 100 ml MDC and distilled out solvent under vacuum below 60° C. The reaction mass was cooled to 25° C. to 35° C. and followed by addition of 250 ml MDC and 200 ml water. The reaction mass was cooled to 10° C. to 15° C. and pH adjusted to 1 to 2 using 20% hydrochloric acid solution and temperature raised to 25° C. to 35° C. Layers were separated and to the MDC layer 200 ml R.O. Water added and cooled to 10° C. to 15° C. and pH adjusted to 9 to 10 using liq ammonia solution and temperature raised to 25° C. to 35° C. Further treated with 5 g charcoal, filtered and washed with 2×50 ml MDC and MDC is distilled out under vacuum below 50° C. to afford the title compound N,N-Diisopropyl-3-(2-benzyloxy-5-bromophenyl)-3-phenylpropylamine of formula (E) in residue form, which is proceeded for next step.

The compound (E) prepared by using water as the solvent instead of neat reaction condition as follows:

100 g 3-(2-(benzyloxy)-5-bromophenyl)-3-phenylpropyl methanesulfonate of formula (D) and 400 ml diisopropyl amine and 100 ml water under closed reaction condition in SSR autoclave for 48 to 50 hours. The reaction mass was cooled to 0° C. to 5° C. followed by filtration and then washing with 25 ml water. After distillation of solvent completely under vacuum and work up with MDC and water in acidic pH and basic afforded title compound N,N-Diisopropyl-3-(2-benzyloxy-5-bromophenyl)-3-phenylpropylamine of formula (E) in residue form.

To 100 g N,N-Diisopropyl-3-(2-benzyloxy-5-bromophenyl)-3-phenylpropylamine of formula (E), 1500 ml IPA and 73.2 g Di-p-toluyl L(−)tartaric acid was added and reaction heated up to 80° C. to 85° C. and then gradually cooled up to 25° C. to 35° C. and maintained for 14 hours and then cooled to 10° C. to 15° C. and then finally filtered and washed with 2×25 ml chilled IPA to afford the p-toluyl-L-tartaric acid salt of N,N-Diisopropyl-3-(2-benzyloxy-5-bromophenyl)-3-phenylpropylamine of formula (E).

To the obtained p-toluyl-L-tartaric acid salt of N,N-Diisopropyl-3-(2-benzyloxy-5-bromophenyl)-3-phenylpropylamine of formula (E) added 500 ml R.O. Water and 300 ml MDC reaction cooled to 0° C. to 5° C. and pH was adjusted at 9 to 10 by 10% sodium hydroxide followed by raising of temperature to 25° C. to 35° C. Layers were separated and MDC layer washed with 2×200 ml 20% brine solution and finally MDC was distilled out under vacuum below 50° C. to afford title compound (R)—N,N-Diisopropyl-3-(2-benzyloxy-5-bromophenyl)-3-Phenylpropylamine compound of formula (F).

Example 3

Preparation of (R)-4-benzyloxy-3-(3-diisopropylamino-1-phenylpropyl)-benzoic acid hydrochloride (G)

To the compound (R)—N,N-Diisopropyl-3-(2-benzyloxy-5-bromophenyl)-3-Phenylpropyl amine compound of formula (F) 25.8 Mg turnings, 400 ml THF, 0.87 g ethyl bromide and 3 crystal of iodine were added and reaction heated to 50° C. to 55° C. and further raised to 65° C. to 70° C. The reaction mass cooled to −60° C. to 70° C. and slowly added 200 g dry ice and stirred for 1 hour. Further the reaction temperature raised to −5° C. to 0° C. followed by slowly addition of 700 ml of 10% ammonium chloride solution. The reaction temperature raised to 25° C. to 35° C., maintained for 30 minutes and finally filtered and washed with 2×25 ml R.O. Water. Layers were separated and further aqueous layer was charged and cooled to 0° C. to 5° C. and adjusted pH at 1 to 2 using conc. Hydrochloric acid solution followed by addition 500 ml MDC. The reaction temperature was raised to 25° C. to 35° C. followed by separation of layers and MDC was distilled under vacuum below at 50° C. The reaction mass was cooled to 25° C. to 35° C. followed by addition of 50 ml of methanol+300 ml of diisopropylether and cooled to 0° C. to 5° C. and finally washed with 2×25 ml diisopropylether to afford the title compound (R)-4-benzyloxy-3-(3-diisopropylamino-1-phenylpropyl)-benzoic acid hydrochloride of formula (G).

Example 4

Preparation of (R)-[4-benzyloxy-3-(3-diisopropylamino-1-phenyl propyl)benzoate

To 250 g 4-benzyloxy-3-(3-diisopropylamino-1-phenyl propyl)benzoate and 2500 ml acetone was heated up to 40° C. to 45° C. and 210.15 g Di-p-toluyl L(−)tartaric acid added and reaction mass was stirred for 2 hours at 40° C. to 45° C. and finally filtered to afford the p-toluyl-L-tartaric acid salt of 4-benzyloxy-3-(3-diisopropylamino-1-phenyl propyl)benzoate.

To the obtained 250 g p-toluyl-L-tartaric acid salt of 4-benzyloxy-3-(3-diisopropylamino-1-phenyl propyl)benzoate added 1250 ml MDC and 750 ml R.O. Water and reaction is cooled to 0° C. to 5° C. and pH is adjusted at 9 to 10 by 10% sodium hydroxide. Layers were separated and and washed with water to afford title compound (R)-[4-benzyloxy-3-(3-diisopropylamino-1-phenyl propyl)benzoate.

Example 5

Preparation of (R)-[4-benzyloxy-3-(3-diisopropylamino-1-phenylpropyl)-phenyl]-methanol (H) Using Vitride from (R)-[4-benzyloxy-3-(3-diisopropylamino-1-phenyl propyl)benzoate

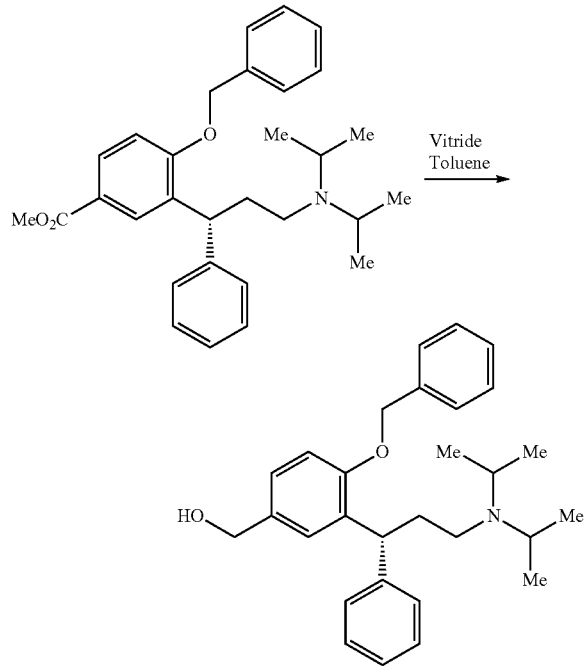

5 gm (R)-[4-benzyloxy-3-(3-diisopropylamino-1-phenyl propyl)benzoate and 25 ml toluene was added under nitrogen atmosphere to a solution of 5.5 g Vitride in 50 ml toluene at 0° C. to 5° C. After stirring at room temperature for 5 hours, methanol was added drop wise at 0° C. to 5° C. After raising the temperature to room temperature, water and toluene was added and stirred for 30 minutes at 25° C. to 35° C. Layers were separated. Toluene layer after complete distillation afforded the title compound as (R)-[4-benzyloxy-3-(3-diisopropylamino-1-phenyl propyl)-phenyl]-methanol of formula (H).

Example 6

Preparation of (R)-[4-benzyloxy-3-(3-diisopropylamino-1-phenylpropyl)-phenyl]-methanol (H) Using Vitride from Acid Compound of Formula (G)

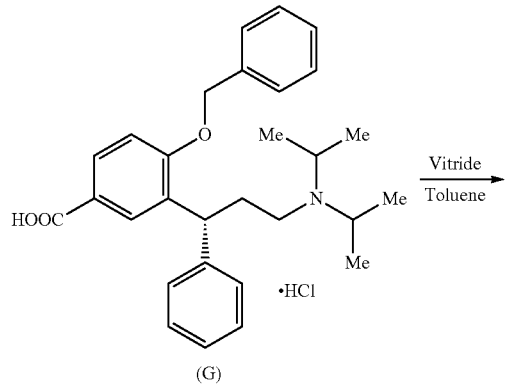

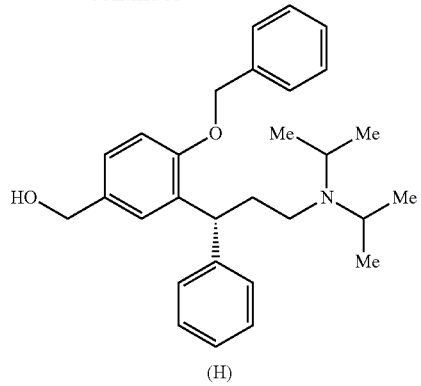

10 g (R)-4-benzyloxy-3-(3-diisopropylamino-1-phenylpropyl)-benzoic acid hydrochloride of formula (G) was added in 10 ml toluene followed by slow addition of 3.2 g Vitride in above solution at 0° C. to 5° C. within 15 minutes. Further 20% HCl solution was added and toluene layer washed with water. Distillation of toluene layer afforded the title compound as (R)-[4-benzyloxy-3-(3-diisopropylamino-1-phenylpropyl)-phenyl]-methanol of formula (H).

Example 7

Preparation of (R)-2-(3-diisopropylamino-1-phenyl-propyl)-4-hydroxy methyl phenol (I)

100 g (R)-[4-Benzyloxy-3-(3-disopropylamino-1-phenylpropyl)-phenyl]-methanol of formula (H) and 100 ml methanol were taken into a Parhydrogenator. Palladium carbon (5%, 20 g) was added and the mixture was hydrogenated with 2-3 kg pressure at 50-55° C. till the completion of reaction. The mixture was then filtered and the solvent was removed by vacuum at below 50° C. The resulting oil was dissolved in 100 ml dichloromethane and the dichloromethane solution was washed with water, and finally crystallized in ethyl acetate and n-hexane to afford the title compound as (R)-2-(3-diisopropylamino-1-phenylpropyl)-4-hydroxy methyl phenol of formula (I).

Example 8

Preparation of (R)—N,N-Diisopropyl-3-(2-benzyloxy-5-bromophenyl)-3-phenylpropyl amine (Fesoterodine) of Formula (J)

100 g (R)-2-(3-Diisopropylamino-1-phenylpropyl)-4-hydroxymethylphenol of formula (I) was added to 2000 ml dichloromethane and cooled to 0° C. This was followed by the addition of a solution of 31.1 g isobutyryl chloride in 100 ml dichloromethane at 0° C. to 5° C. over a period of 1 hour. The contents were stirred for 30 minutes followed by drop wise addition of a solution of 34.5 g triethyl amine in 50 ml of dichloromethane at 0° C. to 5° C. for 30 minutes. The resulting mass was stirred for 30 minutes, 100 ml water was added, separated the layers and washed the dichloromethane layer with 100 ml 5% sodium bicarbonate solution. The dichloromethane layer was dried with sodium sulfate and then distilled off dichloromethane under vacuum to give afford the title compound as Fesoterodine of formula (J).

The compound (J) can be prepared by using inorganic base such sodium carbonate instead of organic base i.e. triethylamine and acetone-water as the solvent as follows:

To 100 g (R)-2-(3-Diisopropylamino-1-phenylpropyl)-4-hydroxymethylphenol of formula (I) was added mixture of 200 ml acetone and 200 ml water and cooled to 0° C. to 5° C. This was followed by the addition of 31 g sodium carbonate and a solution of isobutyryl chloride (neat) within 1 hour at 0° C. to 5° C. The contents were stirred for 15 minutes followed by addition of water (300 ml) and MDC (700 ml) and stirred for 30 minutes. Layers were separated and organic layer was washed with 5% sodium bicarbonate and finally washed with water at 0° C. to 5° C. MDC layer was dried with sodium sulfate and distilled off to afford title compound as Fesoterodine of formula (J).

Example 9

Preparation of Fesoterodine Fumarate of Formula (1)

A solution of 42 g Fesoterodine of formula (J) in 90 ml methyl ethyl ketone was stirred with 12 g fumaric acid at 80° C. for 1 hour. This was followed by the slow addition of 30 ml cyclohexane under stirring and further stirred for 1 hour at 80° C. The solution was cooled slowly to 25° C. to 30° C. and stirred for 6 hours at the same temperature. The solution was further cooled at 0° C. to 50° C. C and stirred for overnight. The separated solid was filtered and washed with mixture of cyclohexane and methyl ethyl ketone mixture to give fesoterodine fumarate.

Example 10

Preparation of (R)-[4-benzyloxy-3-(3-diisopropylamino-1-phenylpropyl)-phenyl]-methanol 5 L Tetrahydrofuran was added in RBF under nitrogen at 25° C. to 35° C. which is cooled to 0° C. to 5° C. followed by addition of Lithium aluminum hydride[7 tablets (0.004 Kg)] initially to quench the residual moisture for THF, wait for 5-10 minutes. Further remaining Lithium aluminum hydride (0.12 Kg) was added slowly portion wise under nitrogen at 0° C. to 5° C. The reaction mass stirred for 15 minutes. Further, solution of FFA-Methyl benzoate (1.0 Kg) and THF (5 L) was added and maintained for 1 hour at 0° C. to 10° C. The reaction mass cooled to 0° C. to 5° C. Very slowly drop wise RO water (100-125 ml) is added in 30-60 minutes under nitrogen atmosphere at 0° C. to 5° C. Further raise the temperature up to 25° C. to 35° C. The reaction mass stirred for 30 minutes. The reaction mass washed with MDC (2×0.50 L). Charge RO water (2.0 L) and MDC (3.0 L) and above obtained reaction mass in RBF and stir for 30 minutes at 25° C. to 35° C. and separate the layers. Take MDC layer and distil out MDC completely atmospheric and finally under vacuum below 50° C. Degas it with methanol (0.50 L) under vacuum at 50° C. to 55° C. to afford the title compound as (R)-[4-benzyloxy-3-(3-diisopropylamino-1-phenylpropyl)-phenyl]-methanol.

Example 11

Preparation of (R)-2-(3-diisopropylamino-1-phenyl-propyl)-4-hydroxy methyl phenol i.e. Compound of Formula (I)

11 L (R)-[4-Benzyloxy-3-(3-diisopropylamino-1-phenyl-propyl)-phenyl]-methanol solution formula (H) and Pd/C (10%, 0.18 Kg) and methanol (30 L) was added in SS autoclave cell at 25° C. to 35° C. and the mixture was hydrogenated with 4 kg pressure at 25° C. to 35° C. for 2 hours. The mixture was then filtered and to the filtrate add 4.1 g sodium borohydride portion wise within 15-30 minutes at 25° C. to 35° C. and stir the reaction mass for 30 minutes. Methanol is distilled out under vacuum below 55° C. Further, reaction mass is cooled to 25° C. to 35° C. Toluene (10.0 L) was added followed by addition of RO water (1.50 L). The reaction mass is heated to 50° C. to 55° C. and maintained for 30 minutes. The layers were separated and to the organic layer add toluene (1.6 L) 25° C. to 35° C. The reaction mass is heated to 65° C. to 70° C. and maintain for 30 minutes. Further cooled to 25° C. to 35° C. and stirred for 2 hours and further cooled to 0° C. to 5° C. and stirred for 30 minutes. The reaction mass is washed with toluene (2×0.25 L) to afford the title compound as (R)-2-(3-diisopropylamino-1-phenylpropyl)-4-hydroxy methyl phenol having impurity X content about 0.03%.

Example 12

Preparation of Fesoterodine Fumarate of Formula (1)

100 g (R)-2-(3-Diisopropylamino-1-phenylpropyl)-4-hydroxymethylphenol of formula (A) was added to 2000 ml dichloromethane and cooled to 0° C. This was followed by the addition of a solution of 31.1 g isobutyryl chloride in 100 ml dichloromethane at 0° C. to 5° C. over a period of 1 hour. The contents were stirred for 30 minutes followed by drop wise addition of a solution of 34.5 g triethyl amine in 50 ml of dichloromethane at 0° C. to 5° C. for 30 minutes. The resulting mass was stirred for 30 minutes, 100 ml water was added, separated the layers and washed the dichloromethane layer with 100 ml 5% sodium bicarbonate solution. The dichloromethane layer was dried with sodium sulfate and then distilled off dichloromethane under vacuum to give afford the title compound as Fesoterodine.

A solution of 42 g Fesoterodine in 90 ml methyl ethyl ketone was stirred with 12 g fumaric acid at 80° C. for 1 hour. This was followed by the slow addition of 30 ml cyclohexane under stirring and further stirred for 1 hour at 80° C. The solution was cooled slowly to 25° C. to 30° C. and stirred for 6 hours at the same temperature. The solution was further cooled at 0° C. to 50° C. C and stirred for overnight. The separated solid was filtered and washed with mixture of cyclohexane and methyl ethyl ketone mixture to give Fesoterodine Fumarate wherein impurity X is 0.03%.

Example 13

Preparation of Fesoterodine 2-chloro-mandelate

Fesoterodine base (5 g) and ethyl acetate (20 ml) were added to a four-neck two liter round bottom flask. Further, 2-chloro-mandelic acid (2.3 g) was added at 25° C. to 35° C. The reaction mass was stirred for 2 hours at 25° C. to 35° C. The reaction mass was cooled to 0° C. to 5° C. The product was filtered and washed with chilled ethyl acetate (2×2.5 ml). The wet cake was dried at 60° C. to 65° C. for 8 to 10 to afford solid fesoterodine 2-chloro-mandelate (Purity by HPLC: 99.8%).

Example 14

Preparation of Fesoterodine Fumarate

Fesoterodine 2-Chloro-mandelate (85 g), water (425 ml) and MDC (225 ml) were added to a four-neck two liter round bottom flask at 25° C. to 35° C. The reaction mass is cooled to 0° C. to 5° C. The pH was adjusted to 10 to 10.5 by addition of 10% sodium hydroxide solution at 0° C. to 5° C. Temperature of the reaction mass is raised to 25° C. to 35° C. and maintained for 30 minutes. The layers were settled and separated. Further, to the MDC layer water (255 ml) is added at 25° C. to 35° C. and further cooled to 0° C. to 5° C. and pH was adjusted to 10 to 10.5 by addition of 10% sodium hydroxide solution. The temperature of the reaction mass is raised to 25° C. to 35° C. and maintained for 30 minutes. The layers were settled and separated. To the MDC layer activated charcoal (4.2 g) is added and stirred for 30 minutes. The resulting mass was filtered and washed with MDC (2×42.5 ml) and to the obtained resulting mass methyl ethyl ketone (170 ml) is added at 25° C. to 30° C. and stirred for 10 minutes and then heated to 80° C. Fumaric acid (21.5 g) was added to the resulting mass, stirred for 1 hour at 80° C. followed by the drop wise addition of cyclohexane (70 ml) at 80° C. and stirred for 1 hour. The resulting mass was slowly cooled to 25° C. to 30° C. and stirred for 12 hours at the same temperature. The resulting mass was then cooled to 0° C. to 5° C. and stirred for 12 hours at 0° C. to 5° C. The separated solid was filtered, washed with the mixture of cyclohexane (135 ml) and methyl ethyl ketone (15 ml), and then dried under vacuum at 45° C. to 50° C. to afford Fesoterodine Fumarate (70 g) (Purity by HPLC: 99.95%).

Example 15

Preparation of Fesoterodine Fumarate

Fesoterodine 2-Chloro-mandelate (85 g), water (425 ml) and MDC (225 ml) were added to a four-neck two liter round bottom flask at 25° C. to 35° C. The reaction mass is cooled to 0° C. to 5° C. The pH was adjusted to 10 to 10.5 by addition of 10% sodium hydroxide solution at 0° C. to 5° C. Temperature of the reaction mass is raised to 25° C. to 35° C. and maintained for 30 minutes. The layers were settled and separated. Further, to the MDC layer water (255 ml) is added at 25° C. to 35° C. and further cooled to 0° C. to 5° C. and pH was adjusted to 10 to 10.5 by addition of 10% sodium hydroxide solution. The temperature of the reaction mass is raised to 25° C. to 35° C. and maintained for 30 minutes. The layers were settled and separated. To the MDC layer activated charcoal (4.2 g) is added and stirred for 30 minutes. The resulting mass was filtered and washed with MDC (2×42.5 ml) and to the obtained resulting mass IPA (240 ml) is added at 25° C. to 30° C. and then heated to 50° C. to 55° C. Fumaric acid (17 g) was added to the resulting mass was maintained for 30 minutes and further cooled to 25° C. to 30° C. followed by the addition of diisopropyl ether (840 ml) at 25° C. to 30° C. and maintained for 12 hours. The resulting mass was filtered, washed with diisopropyl ether (2×30 ml) and then dried under vacuum for 24 hours at 45° C. to 50° C. to afford Fesoterodine Fumarate (70 g) (Purity by HPLC: 99.98%).

Examples 16

Preparation of Fesoterodine Fumarate of Formula (1)

A solution of 42 g Fesoterodine of formula (J) in 90 ml methyl ethyl ketone was stirred with 12 g fumaric acid at 80° C. for 1 hour. This was followed by the slow addition of 30 ml cyclohexane under stirring and further stirred for 1 hour at 80° C. The solution was cooled slowly to 25° C. to 30° C. and stirred for 6 hours at the same temperature. The seeding of fesoterodine fumarate was added to the solution. The solution was further cooled at 0° C. to 5° C. The separated solid was filtered and washed with mixture of cyclohexane and methyl ethyl ketone mixture to give Fesoterodine Fumarate.

PSD: D(90) = 270 microns
Stabilty Study for Fesoterodine Fumarate having with D(90) higher than 200 microns

| Sr. No. | Tests | Specification | Initial | 1 Month 40° C. ± 2° C./RH 75% ± 5% | 2 Months 40° C. ± 2° C./RH 75% ± 5% | 3 Months 40° C. ± 2° C./RH 75% ± 5% |
|---|---|---|---|---|---|---|
| 1 | Description | white to off white | White powder | White powder | White powder | White powder |
| 2 | Water by KF(% w/w) | Not more than 1.0% | 0.33 | 0.56 | 0.2 | 0.12 |
| 3 | | | Related substance | | | |
| | i) Diol | Not more than 0.5 | 0.1 | 0.33 | 0.50 | 0.60 |
| | ii) Diester | Not more than 0.15 | 0.05 | 0.04 | 0.05 | 0.06 |
| | iii) Oxidized (RRT 1.37) | Not more than 0.15 | 0.06 | 0.06 | 0.05 | 0.06 |
| | iv) Any individual impurities | Not more than 0.10 | 0.02 | 0.06 | 0.07 | 0.04 |
| | v) Total impurities | Not more than 1.0 | 0.21 | 0.59 | 0.22 | 0.22 |

| Sr. No. | Tests | 1 Month 25° C. ± 2° C./RH 60% ± 5% | 2 Months 25° C. ± 2° C./RH 60% ± 5% | 3 Months 25° C. ± 2° C./RH 60% ± 5% | 1 Month 2 to 8° C. | 2 Months 2 to 8° C. | 3 Months 2 to 8° C. |
|---|---|---|---|---|---|---|---|
| 1 | Description | White powder | White powder | White powder | White powder | White powder | White powder |
| 2 | Water by KF(% w/w) | 0.15 | 0.15 | 0.16 | 0.16 | 0.16 | 0.16 |
| 3 | | Related substance | | | | | |
| | i) Diol | 0.05 | 0.04 | 0.06 | 0.05 | 0.06 | 0.06 |
| | ii) Diester | BQL | BQL | BQL | BQL | BQL | BQL |
| | iii) Oxidized (RRT 1.37) | BQL | BQL | BQL | BQL | BQL | BQL |
| | iv) Any individual impurities | BQL | BQL | BQL | BQL | BQL | BQL |
| | v) Total impurities | 0.05 | 0.04 | 0.06 | 0.05 | 0.06 | 0.06 |

Preparation of Fesoterodine Fumarate of Formula (1)

A solution of 42 g Fesoterodine of formula (J) in 240 ml IPA (240 ml) is added at 25° C. to 30° C. and then heated to 50° C. to 55° C. Fumaric acid (17 g) was added to the resulting mass was maintained for 30 minutes and further cooled to 25° C. to 30° C. followed by the addition of diisopropyl ether (840 ml) at 25° C. to 30° C. and maintained for 12 hours. The resulting mass was filtered, washed with diisopropyl ether (2×30 ml) and then dried under vacuum for 24 hours at 45° C. to 50° C. to afford Fesoterodine Fumarate (70 g) (Purity by HPLC: 99.98%).

Gradient Composition:

| Time (in minutes) | % Buffer | % Acetonitrile |
|---|---|---|
| 0.01 | 85 | 15 |
| 20 | 50 | 50 |
| 30 | 20 | 80 |
| 31 | 85 | 15 |
| 40 | 85 | 15 |

Diluent: Prepare a filtered and degassed mixture of buffer and acetonitrile in the volume ratio of 75:25.

PSD: D(90) = 10 microns
Stabilty Study for Fesoterodine Fumarate having with D(90) less than 200 microns

| Sr. No. | Tests | Specification | Initial | 1 Month 40° C. ± 2° C./RH 75% ± 5% | 2 Months 40° C. ± 2° C./RH 75% ± 5% | 3 Months 40° C. ± 2° C./RH 75% ± 5% |
|---|---|---|---|---|---|---|
| 1 | Description | white to off white | White powder | White powder | White powder | White powder |
| 2 | Water by KF(% w/w) | Not more than 1.0% | 0.2 | 0.12 | 0.12 | 0.12 |
| 3 | | Related substance (by HPLC, % w/w) | | | | |
| | i) Diol | Not more than 0.5 | 0.06 | 0.07 | 0.07 | 0.07 |
| | ii) Diester | Not more than 0.15 | 0.02 | BQL | BQL | BQL |
| | iii) Oxidized (RRT 1.37) | Not more than 0.15 | 0.05 | 0.17 | 0.27 | 0.29 |
| | iv) Any individual impurities | Not more than 0.10 | 0.02 | 0.02 | 0.04 | 0.04 |
| | v) Total impurities | Not more than 1.0 | 0.15 | 0.28 | 0.49 | 0.49 |

| Sr. No. | Tests | 1 Month 25° C. ± 2° C./RH 60% ± 5% | 2 Months 25° C. ± 2° C./RH | 3 Months 25° C. ± 2° C./RH 60% ± 5% | 1 Month 2 to 8° C. | 2 Months 2 to 8° C. | 3 Months 2 to 8° C. |
|---|---|---|---|---|---|---|---|
| 1 | Description | White powder | White powder | White powder | White powder | White powder | White powder |
| 2 | Water by KF(% w/w) | 0.15 | 0.15 | 0.16 | 0.16 | 0.16 | 0.16 |
| 3 | | Related substance (by HPLC, % w/w) | | | | | |
| | i) Diol | 0.09 | 0.09 | 0.09 | 0.06 | 0.06 | 0.06 |
| | ii) Diester | BQL | BQL | BQL | 0.03 | BQL | 0.03 |
| | iii) Oxidized (RRT 1.37) | 0.15 | 0.17 | 0.19 | 0.09 | 0.09 | 0.08 |
| | iv) Any individual impurities | 0.02 | 0.02 | 0.02 | 0.03 | 0.03 | 0.03 |
| | v) Total impurities | 0.26 | 0.26 | 0.26 | 0.21 | 0.21 | 0.21 |

Analytical Example

1) High Performance Liquid Chromatography (HPLC) Method for Determination of Impurity X in Compound (I)

Chromatographic Conditions:

Equipment: Shimadzu LC2010C HPLC system equipped with a UV-VIS detector or equivalent.
Column: Inertsil ODS-3 (250 mm×4.6 mm, 5 µm), Make: GL Sciences Part No: 5020-01732
Flow rate: 1.7 mL/minute
Column oven temp.: 30° C.
Wavelength: 220 nm
Injection volume: 10 µL
Run time: 40 minutes
Preparation of Buffer:
Transfer 1 mL orthophosphoric acid in 1000 mL volumetric flask containing about 500 mL of water and make up the volume with water. Filter through 0.2 µm membrane filter paper.

2) High Performance Liquid Chromatography (HPLC) Method for Determination of Impurity X in Fesoterodine Fumarate of formula (1)

Chromatographic Conditions:

Equipment: Shimadzu LC2010C HPLC system equipped with a wavelength UV-VIS detector or equivalent.
Column: Inertsil ODS-3 (250 mm×4.6 mm, 5 µm), Make: GL Sciences Part No: 5020-01732
Flow rate: 1.2 mL/minute
Column oven temp: 30° C.
Wavelength: 220 nm
Injection volume: 10 µL
Run time: 60 minutes
Diluent: Premixed buffer and acetonitrile in the volume ratio of 75:25.
Preparation of Buffer:
Transfer 1 mL orthophosphoric acid in 1000 mL volumetric flask containing about 500 mL of water and make up the volume with water. Filter through 0.2 µm membrane filter paper.

Gradient Composition:

| Time (in minutes) | % Buffer | % Acetonitrile |
|---|---|---|
| 0.01 | 75 | 25 |
| 35 | 55 | 45 |
| 50 | 25 | 75 |
| 51 | 75 | 25 |
| 60 | 75 | 25 |

Example 3

Impurity Profile Determination of Fesoterodine Fumarate or Fesoterodine Fumarate Technical

| HPLC | | | |
|---|---|---|---|
| Column & Packing: | Kromasil LC2010C HPLC system equipped with a UV-VIS detector or equivalent | | |
| Eluent A: | Buffer | | |
| Eluent B: | Acetonitrile | | |
| Gradient of Eluent: | Time (min) | Eluent A (%) | Eluent B (%) |
| | 0.01 | 55 | 45 |
| | 35 | 20 | 80 |
| | 50 | 20 | 80 |
| | 51 | 55 | 45 |
| | 60 | 55 | 45 |
| Stop time: | 60 min | | |
| Flow: | 1.3 mL/minute | | |
| Detector: | 318 nm | | |
| Injection Volume: | 10 μm | | |
| Diluent: | Premixed Buffer and Acetonitrile in the volume ratio of 50:50 | | |
| Column temparture: | 30° C. | | |

Sample Solution Preparation

Weigh accurately and transfer about 25 mg of sample of Fesoterodine Fumarate or Fesoterodine Fumarate (technical) into a 50 mL volumetric flask. Add 5 mL tetrahydrofuran, sonicate to dissolve and make up the volume with diluent. Make fresh two preparations at the time of injection.

Preparation of Buffer:

Transfer 1 mL of orthophosphoric acid in 1000 mL volumetric flask containing about 500 mL water and make up the volume with water. Filter through 0.2 μm membrane filter paper.

Method

Inject sample solutions containing the chromatogram upto the end of gradient. Determine the area of each impurity using suitable integrator.

Calculations: Any impurity in a sample is calculated as follows:

$$\% \text{ Impurity in sample} = \frac{\text{Area impurity in sample}}{\Sigma \text{ Areas of all peaks}} \times 100$$

While, the present invention has been described in terms of its specific embodiments, certain modifications and equivalents will be apparent to those skilled in the art and are intended to be included within the scope of the present invention.

We claim:

1. A process for the preparation of fesoterodine or its pharmaceutically acceptable salt, the process comprising
   a) treating (R)-2-(3-diisopropylamino-1-phenylpropyl)-4-hydroxy methyl phenol of formula (I) with reducing agent to obtain pure compound of formula (I),
   b) condensing pure compound of formula (I) with isobutyryl halide in one or more solvents, optionally in the presence of a base to obtain fesoterodine substantially free of impurity X
   c) optionally, converting fesoterodine substantially free of impurity X to its pharmaceutically acceptable salts.

2. The process as claimed in claim 1, wherein the isobutyryl halide is isobutyryl chloride and isobutyryl bromide.

3. The process as claimed in claim 1, wherein the base is organic or inorganic base, which involves triethyl amine, diisopropyl amine, diisopropyl ethyl amine, sodium carbonate, potassium carbonate.

4. A process for the preparation of (R)-2-(3-(Diisopropylamino)-1-phenylpropyl)-4-(hydroxymethyl)phenol compound of formula (I), substantially free of impurity X at RRT about 1.3 having molecular mass 339, the process comprising:
   a) adding a reducing agent to solution of compound of formula (I);
   b) heating the reaction mass;
   c) cooling the reaction mass;
   d) isolating highly pure compound of formula (I).

5. The process as claimed in claim 1, wherein the reducing agent is sodium borohydride, sodium cyanoborohydride, sodium bis(2-methoxyethoxy)aluminium hydride, lithium borohydride, potassium borohydride.

6. A process for the preparation of fesoterodine and its pharmaceutical acceptable salt, the process comprising:
   (a) reacting 6-Bromo-4-phenylchroman-2-one of formula (A) with benzyl chloride to obtain a methyl 3-(2-benzyloxy)-5-bromophenyl)-3-phenylpropanoate compound of formula (B);
   (b) reducing the compound of formula (B) to obtain a 3-(2-(benzyloxy)-5-bromophenyl)-3-phenylpropan-1-ol of formula (C);
   (c) activating compound of formula (C) with methane sulfonyl chloride to obtain 3-(2-(benzyloxy)-5-bromophenyl)-3-phenylpropyl methanesulfonate compound of formula (D), wherein compound of formula (B) and (C) are not isolated;
   (d) reacting compound of formula (D) with diisopropylamine under neat condition or in presence of solvent to obtain 3-(2-(benzyloxy)-5-bromophenyl)-N,N-diisopropyl-3-phenylpropan-1-amine of formula (E);
   (e) resolving 3-(2-(benzyloxy)-5-bromophenyl)-N,N-diisopropyl-3-phenylpropan-1-amine of formula (E) with a suitable optically active acid to obtain (R)—N,N-Diisopropyl-3-(2-benzyloxy-5-bromophenyl)-3-phenylpropyl amine of formula (F);
   (f) reacting (R)—N,N-Diisopropyl-3-(2-benzyloxy-5-bromophenyl)-3-phenylpropyl amine of formula (F) with ethyl halide and Magnesium in presence of solid carbon dioxide to obtain (R)-4-benzyloxy-3-(3-diisopropylamino-1-phenylpropyl)-benzoic acid hydrochloride of formula (G);
   (g) reacting (R)-4-benzyloxy-3-(3-diisopropylamino-1-phenylpropyl)-benzoic acid hydro chloride of formula (G) with Vitride in presence of organic solvent to obtain (R)-[4-benzyloxy-3-(3-diisopropylamino-1-phenylpropyl)-phenyl]-methanol of formula (H);

(h) de-protecting phenyl]-methanol of formula (H) with reducing agent to obtain (R)-2-(3-diisopropylamino-1-phenylpropyl)-4-hydroxy methyl phenol of formula (I);
(i) condensing (R)-2-(3-diisopropylamino-1-phenylpropyl)-4-hydroxy methyl phenol of formula (I) with isobutyryl halide in a suitable solvent, optionally in the presence of base to obtain fesoterodine of formula (J);
(j) optionally, purifying fesoterodine by 2-chloro-mandelate salt formation and
(k) optionally, converting fesoterodine into a pharmaceutically acceptable acid addition salt.

7. A one-pot process for the preparation of 3-(2-(benzyloxy)-5-bromophenyl)-3-phenylpropyl methanesulfonate of formula D, the process comprising:
(a) reacting 6-Bromo-4-phenylchroman-2-one of formula (A) with benzyl chloride to obtain a methyl 3-(2-benzyloxy)-5-bromophenyl)-3-phenylpropanoate compound of formula (B);
(b) reducing the compound of formula (B) to obtain a 3-(2-(benzyloxy)-5-bromophenyl)-3-phenylpropan-1-ol of formula (C); and
(c) activating compound of formula (C) with methane sulfonyl chloride to obtain 3-(2-(benzyloxy)-5-bromophenyl)-3-phenylpropyl methanesulfonate compound of formula (D).

* * * * *